(12) United States Patent
Masanta et al.

(10) Patent No.: US 11,613,774 B2
(45) Date of Patent: Mar. 28, 2023

(54) QUENCHER AND USE THEREOF

(71) Applicant: SFC CO., LTD., Cheongju-si (KR)

(72) Inventors: Goutam Masanta, Cheongju-si (KR); Bong-Ki Shin, Cheongju-si (KR); Ju-man Song, Cheongju-si (KR); Tea-hee Lee, Cheongju-si (KR); Jong-Tae Je, Cheongju-si (KR)

(73) Assignee: SFC Co., Ltd., Cheongju-si (KR)

( * ) Notice: Subject to any disclaimer, the term of this patent is extended or adjusted under 35 U.S.C. 154(b) by 576 days.

(21) Appl. No.: 16/700,618

(22) Filed: Dec. 2, 2019

(65) Prior Publication Data

US 2020/0224257 A1 Jul. 16, 2020

(30) Foreign Application Priority Data

Dec. 4, 2018 (KR) .................. 10-2018-0154337
Sep. 19, 2019 (KR) .................. 10-2019-0115235

(51) Int. Cl.
| | | |
|---|---|---|
| *C12Q 1/68* | (2018.01) | |
| *C09B 23/00* | (2006.01) | |
| *C12Q 1/6844* | (2018.01) | |
| *C07D 519/00* | (2006.01) | |
| *C12Q 1/6806* | (2018.01) | |
| *C12Q 1/686* | (2018.01) | |
| *G01N 33/542* | (2006.01) | |

(52) U.S. Cl.
CPC ......... *C12Q 1/6844* (2013.01); *C07D 519/00* (2013.01); *C12Q 1/6806* (2013.01); *C12Q 1/686* (2013.01); *G01N 33/542* (2013.01)

(58) Field of Classification Search
CPC .... C12Q 1/6844; C12Q 1/6806; C12Q 1/686; C09B 23/00; C09B 23/04; C09B 23/06; C09B 23/08; C09B 23/083
See application file for complete search history.

(56) References Cited

FOREIGN PATENT DOCUMENTS

KR  10-2017-0003984 A  1/2017
KR  10-2017-0101360 A  9/2017

*Primary Examiner* — Jezia Riley
(74) *Attorney, Agent, or Firm* — Studebaker & Brackett PC

(57) ABSTRACT

The present disclosure relates to a quencher having a quenching effect on a fluorescent material exhibiting luminescence characteristics at an excited energy level, and various uses thereof.

15 Claims, 3 Drawing Sheets
Specification includes a Sequence Listing.

QUENCHER AND USE THEREOF

REFERENCE TO AN ELECTRONIC SEQUENCE LISTING

The contents of the electronic sequence listing (sequence_listing.txt; Date of Creation: Mar. 16, 2020; and Size: 2,547 bytes) is herein incorporated by reference in its entirety.

CROSS-REFERENCE TO RELATED APPLICATION

This application claims priority to and the benefit of Korean Patent Application No. 10-2018-0154337, filed on Dec. 4, 2018, and Korean Patent Application No. 10-2019-0115235, filed on Sep. 19, 2019, the disclosures of which are incorporated herein by reference in their entirety.

BACKGROUND

1. Field of the Invention

The present invention relates to a quencher having a quenching effect on a fluorescent material exhibiting luminescence characteristics at an excited energy level, and various uses thereof.

This research was supported by a grant from the Advanced Technology Center (ATC) Program (10076988, Development of fluorescent materials and their application technologies for molecular diagnosis) funded by the Ministry of Trade, Industry & Energy of the Republic of Korea.

2. Discussion of Related Art

A quencher means a molecule capable of quenching the fluorescence of a fluorescent molecule, and a dye having a property capable of absorbing light is generally used.

Mechanisms of quenching phenomenon are known to occur through aggregation of dyes such as fluorescence resonance energy transfer (FRET), photo-induced electron transfer, and H-dimer formation.

When a quencher is used to control or quench the fluorescence of the fluorescent dye, it is most important that the range of the absorption wavelength of the quenching dye covers (overlaps) a substantial part or all of the wavelength region of the fluorescent light exhibited by the fluorescent dye.

In order to obtain a quenching effect, the length between the fluorescent dye and the quencher is also important. For example, the number of bases in the case of DNA and the number of amino acids in the case of a peptide/protein are considered. The length of the linker labeled with the fluorescent dye and the quencher may be adjusted to achieve a higher quenching effect.

In the case of a quencher mainly used commercially in the field of biotechnology, a combination of fluorescence-fluorescent dyes utilizing the FRET phenomenon has been widely used, although a dye structure which cannot emit but only absorb light is generally selected. Such combined fluorescence-quenching and fluorescence-fluorescent dyes are able to impart a kind of on/off function of fluorescence because the original fluorescence thereof is either restored or strengthened when the distances between the fluorescence-quenching and fluorescence-fluorescent dyes recede from each other or biomolecules are separated from each other. These properties have been widely used in designing biosensors or activation probes capable of responding to biomarkers such as specific proteins/enzymes.

When fluorescent or quenching dyes used in the biotechnology field are used alone, they are limited to only FDA-approved dyes, such as indocyanine green or methylene blue, and generally have reactive groups capable of binding to the substituents of biomolecules. Although a variety of the reactive groups have been known, they have been verified for a long time by researchers with respect to a high degree of substituent selectivity, reaction rate, yield, reproducibility, stability, and the like. In recent years, the reactive groups introduced into dyes for practical research or commercial purposes have been limited to several types.

For example, the most frequently used reactive groups for binding of protein molecules with amine groups are succinimidyl ester and isothiocyanate, and the most frequently used reactive groups for binding of protein molecules with thiol groups are maleimide. In addition, dichlorotriazine is mainly used as the reactive group for binding of protein molecules with hydroxy groups.

However, most of the reactive groups have difficulty in maintaining a long-term reaction and storage stability under a water-soluble condition or in a substitution reaction.

SUMMARY

It is an object of the present invention to provide a novel quencher as a compound that can be widely used for observing the identification of biomolecules in the field of optical imaging.

In addition, it is another object of the present invention to provide an oligonucleotide, a composition, and a support for detecting a nucleic acid, which include the above-described novel quencher, and a method for detecting a nucleic acid.

According to one aspect of the present invention for solving the above-described technical problem, there is provided a quencher represented by Chemical Formula 1 below.

[Chemical Formula 1]

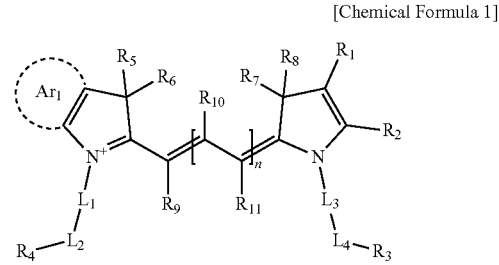

wherein $R_1$ and $R_2$ are bonded to a and b, b and c, or c and d of Chemical Formula 2 below, respectively,

[Chemical Formula 2]

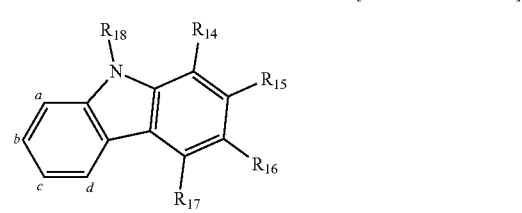

$Ar_1$ is selected from a substituted or unsubstituted aryl, a substituted or unsubstituted heteroaryl, and Chemical Formula 2, n is an integer of 1 to 3, $R_3$ to $R_{18}$ are each independently selected from: a functional group selected from hydrogen, deuterium, a substituted or unsubstituted $C_1$-$C_{10}$ alkyl, a substituted or unsubstituted $C_1$-$C_{10}$ heteroalkyl including at least one heteroatom, a substituted or unsubstituted $C_2$-$C_{10}$ alkenyl, a substituted or unsubstituted $C_2$-$C_{10}$ alkynyl, a substituted or unsubstituted $C_1$-$C_{10}$ alkoxy, a substituted or unsubstituted aryloxy, a substituted or unsubstituted $C_1$-$C_{10}$ haloalkyl, a halogen, a cyano, a hydroxy, a substituted or unsubstituted amino, a substituted or unsubstituted amide, a carbamate, a sulfhydryl, a nitro, a carboxyl, a carboxylate, a substituted or unsubstituted aryl, a substituted or unsubstituted heteroaryl, a substituted or unsubstituted aralkyl, quaternary ammonium, phosphoric acid, a phosphate, a substituted ketone, an aldehyde, a substituted ester, a substituted sulfonyl, a substituted or unsubstituted sulfonamide, an acyl chloride, a sulfonic acid, a sulfonate, hydrazine, a thiol, an acetal, a ketal, a phosphonate (a phosphite), a hypophosphite, sulfohydroxy, a sulfate, azido, guanidium, a ketene, a thiocarbonyl, an aminothiocarbonyl, a polyalkylene oxide, a carboxyl, a carboxyl derivative, a hydroxyl, a haloalkyl, a dienophile, an aldehyde, a ketone, a sulfonyl halide, a thiol, an amine, a sulfhydryl, an alkene, an epoxide, and a phosphoramidite; or a reactive group capable of covalently bonding to the functional group, $R_5$ and $R_6$ are each independently present or linked to each other to form a ring, $R_7$ and $R_8$ are each independently present or linked to each other to form a ring, $L_1$ and $L_3$ are single bonds or linkers including 1 to 40 non-hydrogen atoms, and $L_2$ and $L_4$ are linkers including 1 to 40 non-hydrogen atoms, and At least one substituent among $R_3$ to $R_{18}$ and $Ar_1$ is a functional group selected from a carboxyl, a carboxyl derivative, a hydroxyl, a haloalkyl, a dienophile, an aldehyde, a ketone, a sulfonyl halide, a thiol, an amine, a sulfhydryl, an alkene, an epoxide, and a phosphoramidite or a reactive group capable of covalently bonding to the functional group.

In addition, according to another aspect of the present invention, there is provided an oligonucleotide including the above-described quencher, a minor groove binder (MGB), and a fluorophore.

Additionally, according to still another aspect of the present invention, there is provided a composition for detecting a nucleic acid including the above-described oligonucleotide.

In addition, according to yet another aspect of the present invention, there is provided a support for detecting a nucleic acid including the above-described quencher, a support, and a linker connecting the quencher and the support.

Additionally, according to yet another aspect of the present invention, there is provided a method for detecting a nucleic acid, which includes the steps of: (a) preparing a reaction mixture including a target nucleic acid, a reagent necessary for amplifying the target nucleic acid, and an oligonucleotide; (b) amplifying the target nucleic acid in the reaction mixture by a polymerase chain reaction; and (c) measuring the fluorescence intensity of the reaction mixture.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION

Figure 1:
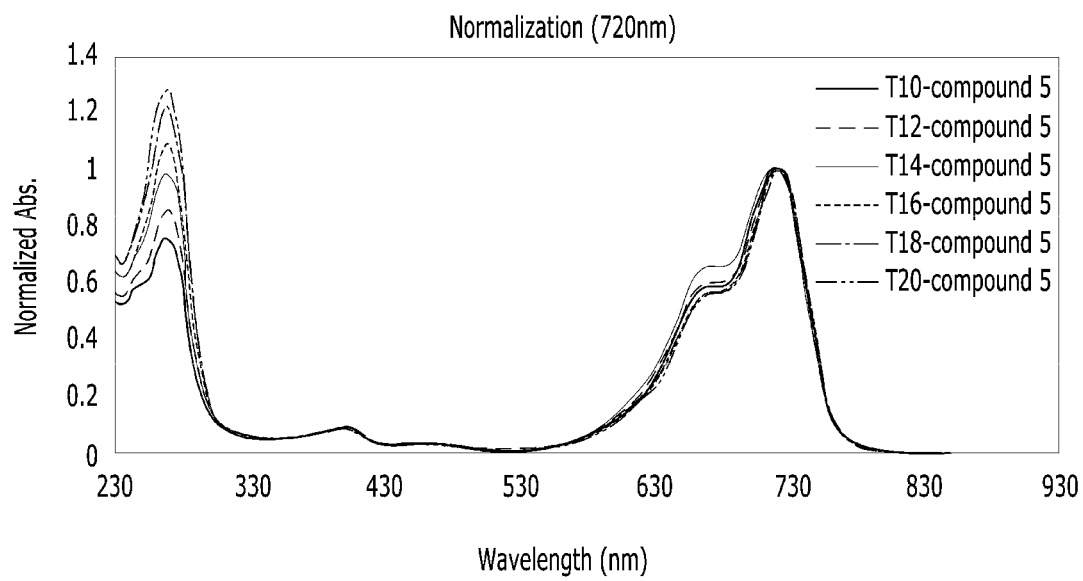
FIG. 1 shows an absorption spectrum of an oligonucleotide including a quencher according to an embodiment of the present invention.

In order to facilitate a better understanding of the present invention, certain terms are defined herein for the purpose of convenience. Unless otherwise defined herein, the scientific and technical terms used herein may have the meaning as commonly appreciated by a person who has an ordinary knowledge in the relevant art.

Also, unless the context clearly indicates otherwise, the singular form of terms may refer to plural forms thereof, and the plural forms of the terms may mean the singular form thereof.

Novel Quencher

According to one aspect of the present invention, there is provided a quencher represented by Chemical Formula 1 below.

[Chemical Formula 1]

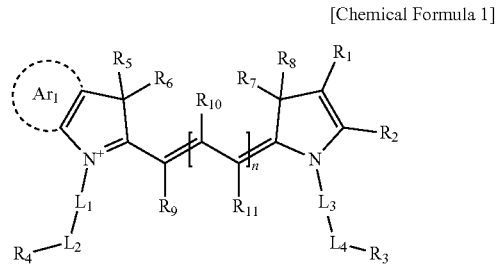

wherein $R_1$ and $R_2$ are bonded to a and b, b and c, or c and d of Chemical Formula 2 below, respectively,

[Chemical Formula 2]

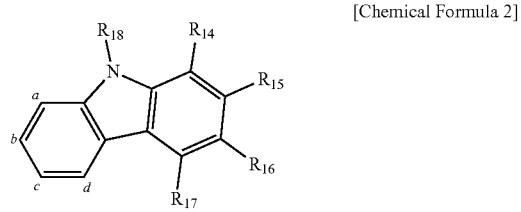

Ar$_1$ is selected from a substituted or unsubstituted aryl, a substituted or unsubstituted heteroaryl, and Chemical Formula 2, n is an integer of 1 to 3, R$_3$ to R$_{18}$ may each independently be selected from: a functional group selected from hydrogen, deuterium, a substituted or unsubstituted C$_1$-C$_{10}$ alkyl, a substituted or unsubstituted C$_1$-C$_{10}$ heteroalkyl including at least one heteroatom, a substituted or unsubstituted C$_2$-C$_{10}$ alkenyl, a substituted or unsubstituted C$_2$-C$_{10}$ alkynyl, a substituted or unsubstituted C$_1$-C$_{10}$ alkoxy, a substituted or unsubstituted aryloxy, a substituted or unsubstituted C$_1$-C$_{10}$ haloalkyl, a halogen, a cyano, a hydroxy, a substituted or unsubstituted amino, a substituted or unsubstituted amide, a carbamate, a sulfhydryl, a nitro, a carboxyl, a carboxylate, a substituted or unsubstituted aryl, a substituted or unsubstituted heteroaryl, a substituted or unsubstituted aralkyl, quaternary ammonium, phosphoric acid, a phosphate, a substituted ketone, an aldehyde, a substituted ester, a substituted sulfonyl, a substituted or unsubstituted sulfonamide, an acyl chloride, a sulfonic acid, a sulfonate, hydrazine, a thiol, an acetal, a ketal, a phosphonate (a phosphite), a hypophosphite, sulfohydroxy, a sulfate, azido, guanidium, a ketene, a thiocarbonyl, an aminothiocarbonyl, a polyalkylene oxide, a carboxyl, a carboxyl derivative, a hydroxyl, a haloalkyl, a dienophile, an aldehyde, a ketone, a sulfonyl halide, a thiol, an amine, a sulfhydryl, an alkene, an epoxide, and a phosphoramidite; or a reactive group capable of covalently bonding to the functional group.

In addition, R$_5$ and R$_6$ among R$_3$ to R$_{18}$ may each independently be present as the above-described functional groups and, in some embodiments, may be linked to each other to form a ring (e.g., a 4-membered ring, a 5-membered ring, a 6-membered ring, a ring consisting of 6 or more atoms, a fused ring in which a plurality of rings are bonded, or the like).

Additionally, R$_7$ and R$_8$ among R$_3$ to R$_{18}$ may each independently be present as the above-described functional groups and, in some embodiments, may be linked to each other to form a ring (e.g., a 4-membered ring, a 5-membered ring, a 6-membered ring, a ring consisting of 6 or more atoms, a fused ring in which a plurality of rings are bonded, or the like).

In another embodiment, R$_5$ and R$_6$ and R$_7$ and R$_8$ among R$_3$ to R$_{18}$ may be linked to each other to form a ring (e.g., a 4-membered ring, a 5-membered ring, a 6-membered ring, a ring consisting of 6 or more atoms, a fused ring in which a plurality of rings are bonded, or the like).

In this case, when R$_5$ and R$_6$ and/or R$_7$ and R$_8$ are linked to each other to form a ring, any carbon in the ring may be substituted with at least one selected from: a functional group selected from deuterium, a substituted or unsubstituted C$_1$-C$_{40}$ alkyl, a substituted or unsubstituted C$_1$-C$_{40}$ heteroalkyl including at least one heteroatom, a substituted or unsubstituted C$_2$-C$_{40}$ alkenyl, a substituted or unsubstituted C$_2$-C$_{40}$ alkynyl, a substituted or unsubstituted C$_1$-C$_{40}$ alkoxy, a substituted or unsubstituted aryloxy, a substituted or unsubstituted C$_1$-C$_{40}$ haloalkyl, a halogen, a cyano, a hydroxy, a substituted or unsubstituted amino, a substituted or unsubstituted amide, a carbamate, a sulfhydryl, a nitro, a carboxyl, a carboxylate, a substituted or unsubstituted aryl, a substituted or unsubstituted heteroaryl, a substituted or unsubstituted aralkyl, quaternary ammonium, phosphoric acid, a phosphate, a substituted ketone, an aldehyde, a substituted ester, a substituted sulfonyl, a substituted or unsubstituted sulfonamide, an acyl chloride, a sulfonic acid and a sulfonate, a substituted or unsubstituted C$_1$-C$_{40}$ alkylthio, a substituted or unsubstituted arylthio, a substituted or unsubstituted C$_3$-C$_{20}$ cycloalkyl, a substituted or unsubstituted C$_1$-C$_{20}$ heterocycloalkyl including at least one heteroatom, a substituted or unsubstituted C$_3$-C$_{20}$ cycloalkenyl, a substituted or unsubstituted C$_2$-C$_{20}$ heterocycloalkenyl including at least one heteroatom, a substituted or unsubstituted silyl, substituted or unsubstituted germanium, an ether, a nitrile, a polyalkylene oxide, a carboxyl, a carboxyl derivative, a hydroxyl, a haloalkyl, a dienophile, an aldehyde, a ketone, a sulfonyl halide, a thiol, an amine, a sulfhydryl, an alkene, an epoxide, and a phosphoramidite; and a reactive group capable of covalently bonding to the functional group.

L$_1$ and L$_3$ are single bonds or linkers including 1 to 40 non-hydrogen atoms, and L$_2$ and L$_4$ are linkers including 1 to 40 non-hydrogen atoms. Here, the linker including a non-hydrogen atom refers to a group consisting of a bond of atoms such as carbon, nitrogen, oxygen, and the like rather than hydrogen. Accordingly, the linker may include a chain and/or ring (e.g., an aromatic ring and/or an aliphatic ring) consisting of a bond of non-hydrogen atoms such as carbon, nitrogen, oxygen, and the like.

At least one substituent among R$_3$ to R$_{18}$ and Ar$_1$ is a functional group selected from a carboxyl, a carboxyl derivative, a hydroxyl, a haloalkyl, a dienophile, an aldehyde, a ketone, a sulfonyl halide, a thiol, an amine, a sulfhydryl, an alkene, an epoxide, and a phosphoramidite or a reactive group capable of covalently bonding to the functional group. In particular, at least one of R$_3$ and R$_4$ may be a functional group selected from a carboxyl, a carboxyl derivative, a hydroxyl, a haloalkyl, a dienophile, an aldehyde, a ketone, a sulfonyl halide, a thiol, an amine, a sulfhydryl, an alkene, an epoxide, and a phosphoramidite or a reactive group capable of covalently bonding to the functional group.

Examples of the reactive group include: (a) a carboxyl group and a derivative thereof: N-hydroxysuccinimide ester, N-hydroxybenzotriazole ester, an acyl halide, acyl imidazole, thioester, p-nitrophenyl ester, alkyl ester, alkenyl ester, alkynyl ester, and aromatic ester; (b) a hydroxyl which may be converted to an ester, an ether, or an aldehyde; (c) a haloalkyl which may be covalently attached to another functional group by substituting a halogen with a nucleophilic functional group such as an amine, a carboxylate anion, a thiol anion, a carbo anion, or an alkoxide ion; (d) a dienophile capable of carrying out a Diels-Alder reaction, for example, with a maleimide group; (e) an aldehyde or ketone capable of forming a carbonyl derivative such as imine, hydrazone, semicarbazone, or oxime; (f) a sulfonyl halide which reacts with an amine to form a sulfoamide; (g) a thiol which is converted to a disulfide or is capable of reacting with an acyl halide; (h) an amine or sulfhydryl which may be acylated, alkylated, or oxidized; (i) an alkene capable of carrying out reactions such as cycloaddition, acylation, the Michael reaction, and the like; (j) an epoxide capable of reacting with an amine or a hydroxyl compound; (k) a phosphoramidite and other standard functional groups useful for the nucleic acid reactions, and the like. These reactive groups can be appropriately selected so as not to participate in or interfere with the reaction needed to synthesize the reactive quencher.

In another embodiment, such a reactive group may be protected by a protecting group such that the reactive group does not participate in any reaction in the presence of the protecting group. For example, when the reactive group is hydroxyl, the protecting group may be trialkylsilyl, 4,4-dimethoxytrityl or an analog thereof. Examples of preferred protecting groups can be found in the following reference (Greene et al., PROTECTIVE GROUPS IN ORGANIC SYNTHESIS, John Wiley & Sons, New York, 1991).

The quencher according to various embodiments of the present invention may label by binding with the target biomolecule (e.g., nucleic acid) through the above-described reactive group.

The above-described reactive groups are functional groups capable of reacting with a functional group such as an amino group, imino group, thiol group, hydroxyl group, or the like of the target biomolecule, and may form a covalent bond such as an amide bond, an imide bond, a urethane bond, an ester bond, a phosphite bond, a phosphate bond, or a guanidine bond between the quencher and the target biomolecule.

In addition, $R_1$ and $R_2$ may be bonded to a and b, b and c, or c and d of Chemical Formula 2, respectively. For example, $R_1$ may be bonded to a of Chemical Formula 2, $R_2$ may be bonded to b of Chemical Formula 2, and vice versa.

In addition, when any functional group among $R_3$ to $R_{18}$ is substituted, any carbon in the functional group may be substituted with at least one selected from: a functional group selected from deuterium, a substituted or unsubstituted $C_1$-$C_{40}$ alkyl, a substituted or unsubstituted $C_1$-$C_{40}$ heteroalkyl including at least one heteroatom, a substituted or unsubstituted $C_2$-$C_{40}$ alkenyl, a substituted or unsubstituted $C_2$-$C_{40}$ alkynyl, a substituted or unsubstituted $C_1$-$C_{40}$ alkoxy, a substituted or unsubstituted aryloxy, a substituted or unsubstituted $C_1$-$C_{40}$ haloalkyl, a halogen, a cyano, a hydroxy, a substituted or unsubstituted amino, a substituted or unsubstituted amide, a carbamate, a sulfhydryl, a nitro, a carboxyl, a carboxylate, a substituted or unsubstituted aryl, a substituted or unsubstituted heteroaryl, a substituted or unsubstituted aralkyl, quaternary ammonium, phosphoric acid, a phosphate, a substituted ketone, an aldehyde, a substituted ester, a substituted sulfonyl, a substituted or unsubstituted sulfonamide, an acyl chloride, a sulfonic acid and a sulfonate, a substituted or unsubstituted $C_1$-$C_{40}$ alkylthio, a substituted or unsubstituted arylthio, a substituted or unsubstituted $C_3$-$C_{20}$ cycloalkyl, a substituted or unsubstituted $C_1$-$C_{20}$ heterocycloalkyl including at least one heteroatom, a substituted or unsubstituted $C_3$-$C_{20}$ cycloalkenyl, a substituted or unsubstituted $C_2$-$C_{20}$ heterocycloalkenyl including at least one heteroatom, a substituted or unsubstituted silyl, substituted or unsubstituted germanium, an ether, a nitrile, a polyalkylene oxide, a carboxyl, a carboxyl derivative, a hydroxyl, a haloalkyl, a dienophile, an aldehyde, a ketone, a sulfonyl halide, a thiol, an amine, a sulfhydryl, an alkene, an epoxide, and a phosphoramidite; and a reactive group capable of covalently bonding to the functional group.

In the specification, when Ra is an alkenyl or alkynyl, the $sp^2$-hybrid carbon of the alkenyl or the sp-hybrid carbon of the alkynyl may be in the form bonded either directly or indirectly by the $sp^3$-hybrid carbon of an alkyl which is bonded to the $sp^2$-hybrid carbon of the alkenyl or the sp-hybrid carbon of the alkynyl.

In the specification, the $C_a$-$C_b$ functional group refers to a functional group having a to b carbon atoms. For example, a $C_a$-$C_b$ alkyl means a saturated aliphatic group including a straight chain alkyl and a branched chain alkyl having a to b carbon atoms. The straight chain or branched chain alkyl may have 40 or less carbon atoms in its main chain (e.g., a straight chain of $C_1$-$C_{10}$, branched chain of a $C_3$-$C_{10}$).

Specifically, the alkyl may be methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethylet-1-yl, n-hexyl, n-heptyl, or n-octyl.

In the specification, alkoxy refers to both of —O— (alkyl) group and —O— (unsubstituted cycloalkyl) group and is a straight chain or branched chain hydrocarbon having one or more ether groups and 1 to 10 carbon atoms.

Specifically, examples of the alkoxy include methoxy, ethoxy, propoxy, isopropoxy, n-butoxy, tert-butoxy, sec-butoxy, n-pentoxy, n-hexoxy, 1,2-dimethylbutoxy, cyclopropyloxy, cyclobutyloxy, cyclopentyloxy, cyclohexyloxy, and the like, but the present invention is not limited thereto.

In the specification, halogen refers to fluoro (—F), chloro (—Cl), bromo (—Br), or iodo (—I), and haloalkyl means an alkyl substituted with a halogen as described above. For example, halomethyl means methyl (—CH$_2$X, —CHX$_2$, or —CX$_3$) in which at least one of the hydrogens in methyl is replaced with a halogen.

In the specification, aralkyl refers to a functional group in which an aryl is substituted to a carbon of the alkyl, and is a general term for —(CH$_2$)$_n$Ar. Examples of the aralkyl include benzyl (—CH$_2$C$_6$H$_5$) and phenethyl (—CH$_2$CH$_2$C$_6$H$_5$).

Unless otherwise defined herein, aryl means an unsaturated aromatic ring including a single ring or multiple rings (preferably one to four rings) joined together or covalently bonded to each other. Non-limiting examples of aryl include phenyl, biphenyl, o-terphenyl, m-terphenyl, p-terphenyl, 1-naphthyl, 2-naphthyl, 1-anthryl, 2-anthryl, 9-anthryl, 1-phenanthrenyl, 2-phenanthrenyl, 3-phenanthrenyl, 4-phenanthrenyl, 9-phenanthrenyl, 1-pyrenyl, 2-pyrenyl, 4-pyrenyl, and the like.

In the specification, heteroaryl refers to a functional group in which one or more carbon atoms in the aryl as defined above are substituted with a non-carbon atom such as nitrogen, oxygen or sulfur. Non-limiting examples of heteroaryl include furyl, tetrahydrofuryl, pyrrolyl, pyrrolidinyl, thienyl, tetrahydrothienyl, oxazolyl, isoxazolyl, triazolyl, thiazolyl, isothiazolyl, pyrazolyl, pyrazolidinyl, oxadiazolyl, thiadiazolyl, imidazolyl, imidazolinyl, pyridyl, pyridaziyl, triazinyl, piperidinyl, morpholinyl, thiomorpholinyl, pyrazinyl, piperainyl, pyrimidinyl, naphthyridinyl, benzofuranyl, benzothienyl, indolyl, indolinyl, indolizinyl, indazolyl, quinolizinyl, quinolinyl, isoquinolinyl, cinnolinyl, phthalazinyl, quinazolinyl, quinoxalinyl, pteridinyl, quinuclidinyl, carbazoyl, acridinyl, phenazinyl, phenothizinyl, phenoxazinyl, purinyl, benzimidazolyl, benzothiazolyl, and the like; and analogs to which they are conjugated.

In the specification, a hydrocarbon ring (cycloalkyl) or a hydrocarbon ring (heterocycloalkyl) including a heteroatom may be understood to be a cyclic structure of an alkyl or heteroalkyl, respectively, unless otherwise defined.

Non-limiting examples of hydrocarbon rings include cyclopentyl, cyclohexyl, 1-cyclohexenyl, 3-cyclohexenyl, cycloheptyl, and the like. Non-limiting examples of hydrocarbon rings including a heteroatom include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothiene-3-yl, 1-piperazinyl, 2-piperazinyl, and the like.

In addition, a hydrocarbon ring or a hydrocarbon ring including a heteroatom may have a form in which a hydrocarbon ring, a hydrocarbon ring including a heteroatom, an aryl or a heteroaryl is bonded or linked thereto by a covalent bond.

In the specification, polyalkylene oxide is an aqueous polymer functional group, and includes polyethylene glycol (PEG), polypropylene glycol (PPG), a polyethylene glycol-polypropylene glycol (PEG-PPG) copolymer, and an N-substituted methacrylamide-containing polymer and copolymer.

The polyalkylene oxide may be additionally substituted as necessary to the extent that the properties of the polymer are maintained. For example, the substitution may be a chemical bond to increase or decrease the chemical or biological stability of the polymer. As a specific example, any carbon or terminal carbon in the polyalkylene oxide may be substituted with hydroxy, alkyl ether (methyl ether, ethyl ether, propyl ether, and the like), carboxylmethyl ether, carboxyethyl ether, benzyl ether, dibenzylmethylene ether, or dimethylamine. In an embodiment, the polyalkylene oxide may be a polyethylene oxide (mPEG) terminated with methyl ether, wherein mPEG is represented by the formula —$(CH_2CH_2O)_nCH_3$, and the size of mPEG may vary depending on the size of n which corresponds to the number of ethylene glycol repeat units.

In addition, the quencher represented by Chemical Formula 1 may have a structure additionally including a counter ion. The counter ion is an organic or inorganic anion and may be appropriately selected in consideration of the solubility and stability of the quencher.

Examples of the counter ion of the quencher according to an embodiment of the present invention include inorganic acid anions such as a phosphoric acid hexafluoride ion, a halogen ion, a phosphoric acid ion, a perchloric acid ion, a periodic acid ion, an antimony hexafluoride ion, a tartaric acid hexafluoride ion, a fluoroboric acid ion, a tetrafluoride ion, and the like; and organic acid ions such as a thiocyanate ion, a benzenesulfonic acid ion, a naphthalenesulfonic acid ion, a p-toluenesulfonic acid ion, an alkylsulfonic acid ion, a benzenecarboxylic acid ion, an alkylcarboxylic acid ion, a trihaloalkylcarboxylic acid ion, an alkyl sulfonic acid ion, a trihaloalkylsulfonic acid ion, a nicotinic acid ion, and the like. In addition, metal compound ions such as bisphenylditol, thiobisphenol chelate, bisdiol-α-diketone, and the like; metal ions such as sodium, potassium, and the like, and quaternary ammonium salts may also be selected as the counter ion.

Specific examples of the quencher represented by Chemical Formula 1 are as follows. The quenchers exemplified below are several examples of the quencher represented by Chemical Formula 1, and the quencher according to the present invention targets a quencher with a basic backbone represented by Chemical Formula 1. That is, it should be understood that not only a quencher exemplified below but also a compound with a basic backbone represented by Chemical Formula 1 has an equal or similar level of a quenching effect on a fluorescent material exhibiting luminescence characteristics at an excited energy level.

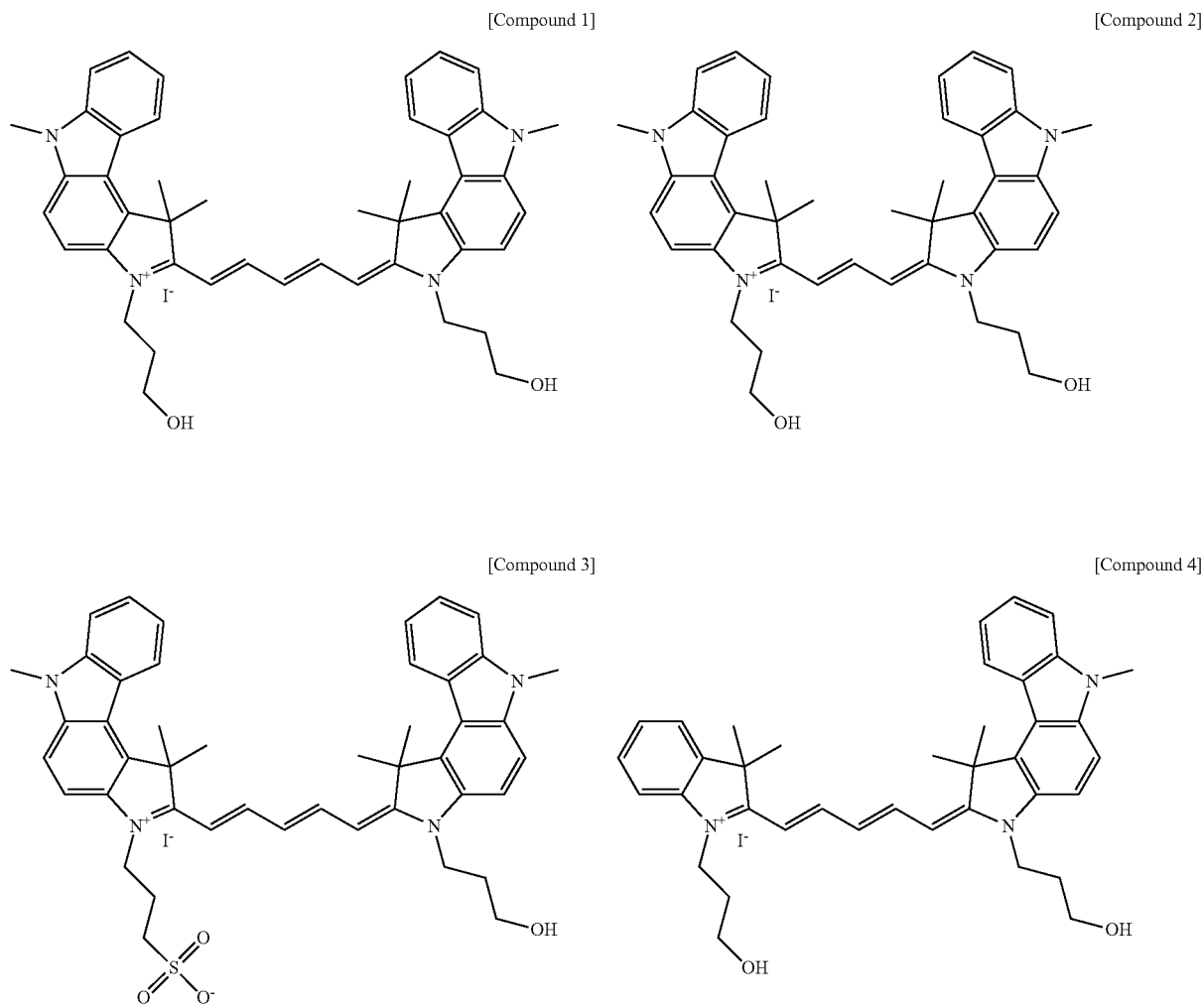

-continued

[Compound 5]

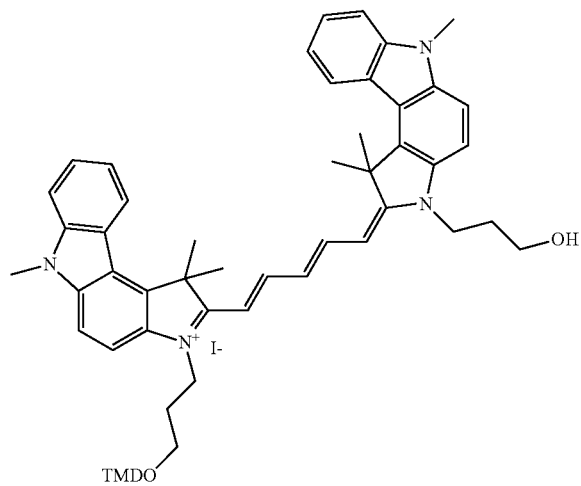

[Compound 6]

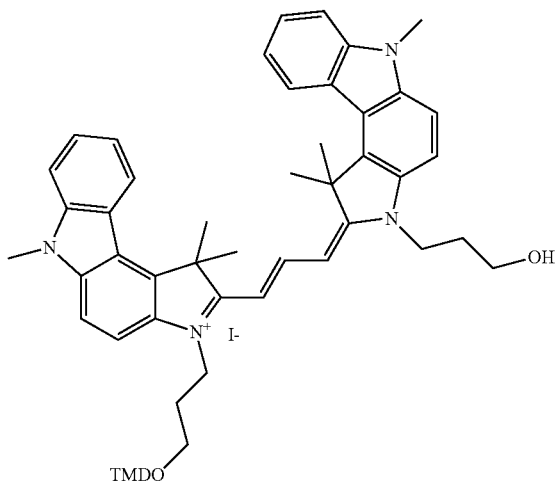

[Compound 7]

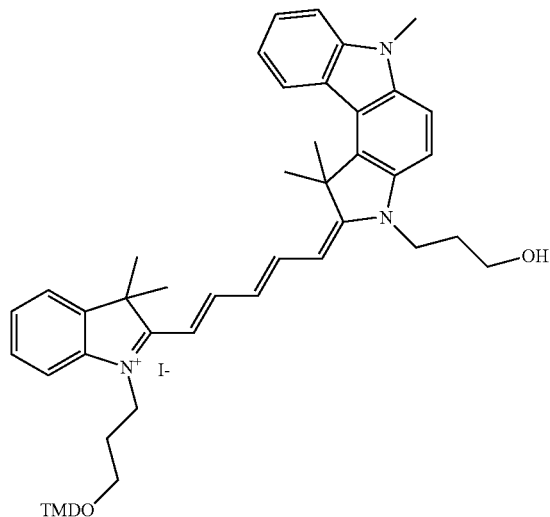

[Compound 8]

[Compound 9]

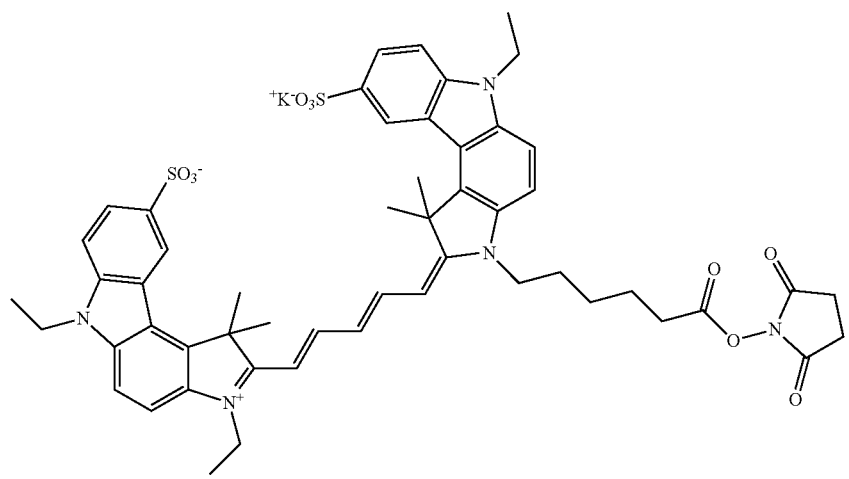

The biomolecule that is the target of the quencher represented by Chemical Formula 1 disclosed herein may be at least one selected from antibodies, lipids, proteins, peptides, carbohydrates and nucleic acids (including nucleotides).

Specific examples of lipids include fatty acids, phospholipids, lipopolysaccharides and the like, and specific examples of carbohydrates include monosaccharides, disaccharides, and polysaccharides (e.g., dextran).

In this case, the biomolecule may be a functional group for reacting with any functional group of the quencher represented by Chemical Formula 1 or with a reactive group bonded to the quencher represented by Chemical Formula 1, and it may include at least one selected from amino, sulfhydryl, carbonyl, hydroxyl, carboxyl, phosphate, and thiophosphate or may have a derivative form thereof.

In addition, the biomolecule may include at least one selected from amino, sulfhydryl, carbonyl, hydroxyl, carboxyl, phosphate, and thiophosphate or may be an oxy or dioxy polynucleic acid having a derivative form thereof.

Furthermore, in addition to the biomolecule, the quencher represented by Chemical Formula 1 may be used to label drugs, hormones (including receptor ligands), receptors, enzymes or enzyme substrates, cells, cell membranes, toxins, microorganisms, nano-bio materials (such as polystyrene microspheres), or the like, which include at least one selected from amino, sulfhydryl, carbonyl, hydroxyl, carboxyl, phosphate and thiophosphate.

Oligonucleotide, Composition for Detecting Nucleic Acid, Support for Detecting Nucleic Acid, which Include Novel Quencher According to another aspect of the present invention, there is provided an oligonucleotide including at least one selected from the quenchers represented by Chemical Formula 1.

The oligonucleotide refers to a polymer of one to several hundred nucleotides and includes all of DNA, RNA, or PNA. In addition, the oligonucleotide encompasses analogs thereof, all that can be easily modified by those skilled in the art, for example, those in which the nucleotide has been chemically modified or those to which the sugar has been conjugated, and all of those with the single- or double strands.

It is preferred that the oligonucleotide includes a probe. More preferably, such a probe is a probe capable of complementarily binding with a target nucleic acid, but the present invention is not limited thereto. Here, the probe may be selected from a nucleic acid, a peptide, a saccharide, an oligonucleotide, a protein, an antibody, or a combination thereof, but the present invention is not limited thereto.

In an embodiment, the oligonucleotide may include a fluorophore. For example, the 5' end of the oligonucleotide may be labeled with the fluorophore, and the 3' end of the oligonucleotide may be labeled with at least one selected from the quenchers represented by Chemical Formula 1. The probe capable of complementarily binding to the target nucleic acid may be located between the 5' end and the 3' end.

For the fluorophore, reference may made to the types of fluorophore disclosed in the following references (Cardullo et al., Proc. Natl. Acad. Sci. USA 85: 8790-8794 (1988); Dexter, D. L., J. of Chemical Physics 21: 836-850 (1953); Hochstrasser et al., Biophysical Chemistry 45: 133-141 (1992); Selvin, P., Methods in Enzymology 246: 300-334 (1995); Steinberg, I. Ann. Rev. Biochem., 40: 83-114 (1971); Stryer, L. Ann. Rev. Biochem., 47: 819-846 (1978); Wang et al., Tetrahedron Letters 31: 6493-6496 (1990); Wang et al., Anal. Chem. 67: 1197-1203 (1995)).

In addition, non-limiting examples of the fluorophore that may be used herein include 4-acetamido-4'-isothiocyanatostilbene-2,2'-disulfonic acid, acridine and derivatives thereof, 5-(2'-aminoethyl)aminonaphthalene-1-sulfonic acid (EDANS), 4-amino-N-[3-vinylsulfonyl)phenyl]naphthalimide-3,5 disulfonate, N-(4-anilino-1-naphthyl)maleimide, anthranilamide, BODIPY, Brilliant Yellow, coumarin (7-amino-4-methylcoumarin (AMC, Coumarin 120), 7-amino-4-trifluoromethylcouluarin (Coumarin 151) and derivatives thereof, cyan dye, cyanosine, 4',6-diaminidino-2-phenylindole (DAPI), 5',5"-dibromopyrogallol-sulfonaphthalein (Bromopyrogallol Red), 7-diethylamino-3-(4'-isothiocyanatophenyl)-4-methylcoumarin, diethylenetriamine pentaacetate, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), 4-(4'-dimethylaminophenylazo) benzoic acid (DABCYL), 4-dimethylaminophenylazophenyl-4'-isothiocyanate (DABITC), eosin and derivatives thereof (eosin isocyanate), erythrosine and derivatives thereof (erythrosine B, erythrosine isocyanate), ethidium, fluorescein and derivatives thereof (5-carboxyfluorescein (FAM)), 5-(4,6-dichlorotriazin-2-yl)aminofluorescein (DTAF), 2',7'-dimethoxy-4'5'-dichloro-6-carboxyfluorescein (JOE), QFITC (XRITC), fluorescamine, IR144, IR1446, Malachite Green isothiocyanate, 4-methylumbelliferone, ortho cresolphthalein, nitrotyrosine, pararosaniline, phenol red, B-phycoerythrin, o-phthaldialdehyde, pyrene and derivatives thereof (pyrenebutyrate, succinimidyl 1-pyrenebutyrate), quantum dots, Reactive Red 4 (Cibacron™ Brilliant Red 3B-A), rhodamine and derivatives thereof (6-carboxy-X-rhodamine, 6-carboxyrhodamine, rhodamine B, rhodamine 123, rhodamine X isocyanate, sulforhodamine B, sulforhodamine 101, tetramethyl rhodamine, tetramethyl rhodamine isocyanate), riboflavin, rosolic acid, pyrene, carbopyronine, oxazine, xanthene, thioxanthene, terbium chelate derivatives, and the like.

In addition, the oligonucleotide according to the present invention may further include a minor groove binder (MGB) to improve bonding strength with a nucleic acid.

Such oligonucleotide can be widely utilized in a variety of chemical and biological fields. In particular, it may be useful for real-time polymerase chain reaction (PCR), microassay, and the like, but the present invention is not limited thereto.

According to still another aspect of the present invention, there is provided a composition for detecting a nucleic acid, which includes the oligonucleotide.

The composition for detecting a nucleic acid according to an embodiment of the present invention may further include an enzyme for reacting with the target biomolecule, a solvent (such as a buffer solution), other reagents, and the like, in addition to the oligonucleotide simultaneously including the quencher represented by Chemical Formula 1, a minor groove binder (MGB), and a fluorophore.

Here, the solvent may be: a buffer solution selected from the group consisting of a phosphate buffer solution, a carbonate buffer solution, and a Tris buffer solution; an organic solvent selected from dimethyl sulfoxide, dimethylformamide, dichloromethane, methanol, ethanol, and acetonitrile; or water. It is possible to control solubility by introducing various functional groups into the quencher depending on the kind of solvent.

According to yet another aspect of the present invention, there is provided a support for detecting a nucleic acid, which includes the quencher represented by Chemical Formula 1, a support, and a linker connecting the quencher and the support.

Accordingly, the biomolecule in the sample may be immobilized on the support matrix through interaction with the quencher immobilized on the support.

The support matrix may be prepared with at least one selected from glass, cellulose, nylon, acrylamide gel, dextran, polystyrene, alginate, collagen, peptides, fibrin, hyaluronic acid, agarose, polyhydroxyethyl methacrylate, polyvinyl alcohol, polyethylene glycol, polyethylene oxide, polyethylene glycol diacrylate, gelatin, Matrigel, polylactic acid, carboxymethylcellulose, dextran, chitosan, latex, and sepharose, and may be in the form of a bead or membrane.

Here, the linker connects the quencher and the support, and any material capable of connecting the quencher and the support may be used as the linker intended herein.

For example, the linker may be selected from a substituted or unsubstituted $C_1$-$C_{30}$ alkyl, a substituted or unsubstituted $C_2$-$C_{30}$ heteroalkyl including at least one heteroatom, a substituted or unsubstituted $C_6$-$C_{30}$ aryl, and a substituted or unsubstituted $C_3$-$C_{30}$ heteroaryl, and more specifically, may be a chain in which 1 to 6 ethylene glycols are linked.

Such a linker connects the quencher and the support only and does not affect other reactions or the fluorescence-quenching of the quencher or the fluorophore.

Method for Detecting Nucleic Acid

According to an embodiment of the present invention, a method for reacting and labeling a probe labeled with a quencher to a target nucleic acid may be implemented. In addition, a method for labeling a biomolecule using a target-specific interaction by introducing an appropriate reactive group into a quencher depending on the kind of target biomolecule may be implemented. Furthermore, a method for identifying a biomolecule labeled with a quencher through electrophoresis may be implemented.

DNA Microarray

In a DNA microarray, a target nucleic acid is labeled by reacting with a dye, meanwhile, a single-stranded probe nucleic acid having a base sequence complementary to the target nucleic acid is prepared, and the target nucleic acid denatured to a single strand and the probe nucleic acid are hybridized on a substrate to measure fluorescence of the target nucleic acid.

In the case of examining the expression of a gene, as the probe nucleic acid immobilized on a substrate in the labeling method, what has been prepared by amplifying a cDNA library, a genomic library, or all genomes as a template through a PCR method, for example, cDNA, may be used.

In addition, in the case of examining a mutation of a gene or the like, the probe nucleic acid may be prepared by synthesizing various oligonucleotides corresponding to the mutation, etc. based on the standard sequence already known.

The immobilization of the probe nucleic acid on the substrate may be performed by a method appropriately selected depending on the kind of nucleic acid or the type of substrate. For example, it is possible to use a method of performing electrostatic bonding to the substrate whose surface is treated with a cation, such as polylysine or the like, using the charge of DNA.

The target nucleic acid denatured to a single strand is immobilized on the substrate and hybridized with the oligonucleotide, whereby the 5' end of the oligonucleotide is labeled with a fluorophore, and the 3' end thereof is labeled with at least one selected from the quenchers represented by Chemical Formula 1. A probe capable of complementarily binding to the target nucleic acid may be located between the 5' end and the 3' end of the oligonucleotide.

The hybridization is preferably performed at room temperature to 70° C. for 2 to 48 hours. By the hybridization, a target nucleic acid having a base sequence complementary to the probe nucleic acid selectively binds to the probe nucleic acid. Thereafter, the substrate is cleaned and dried at room temperature.

In this case, the oligonucleotide is hybridized to the target nucleic acid by the probe, but the fluorophore at the 5' end is in a state of being quenched by the quencher at the 3' end.

Subsequently, the oligonucleotide hybridized to the target nucleic acid is elongated by a polymerase, and separated and cleaved from the target nucleic acid by the exonuclease activity of the polymerase. Therefore, the fluorophore at the 5' end of the oligonucleotide and the quencher at the 3' end thereof are separated from each other, such that the fluorophore may emit fluorescence.

In this case, the intensity of fluorescence to be emitted may be measured to determine the amplification amount of the target nucleic acid.

Hereinafter, specific embodiments of the present invention will be described. It should be understood that the examples described below are for illustrating or explaining the present invention only, but are not intended to be limiting the present invention.

Preparation Example 1. Synthesis of Compound 5

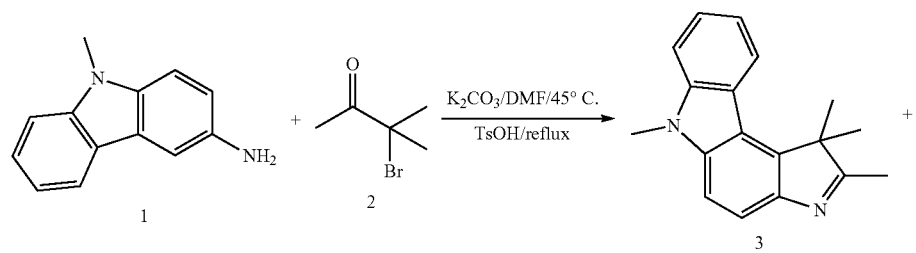

-continued
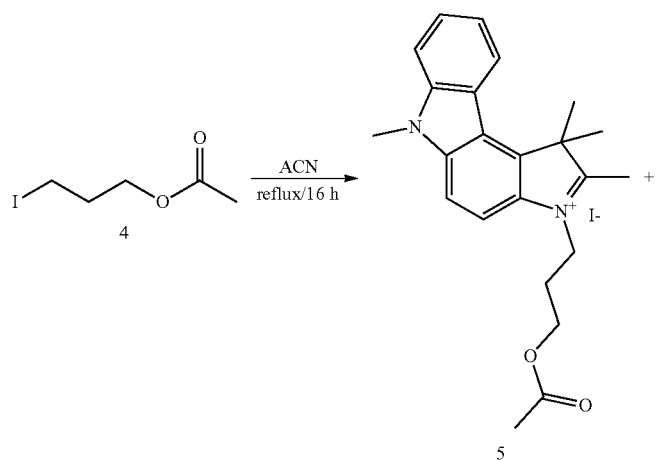
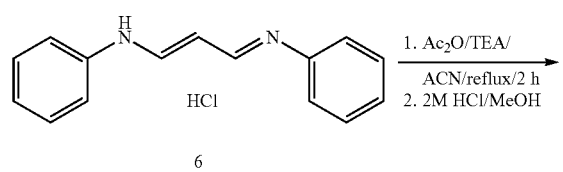
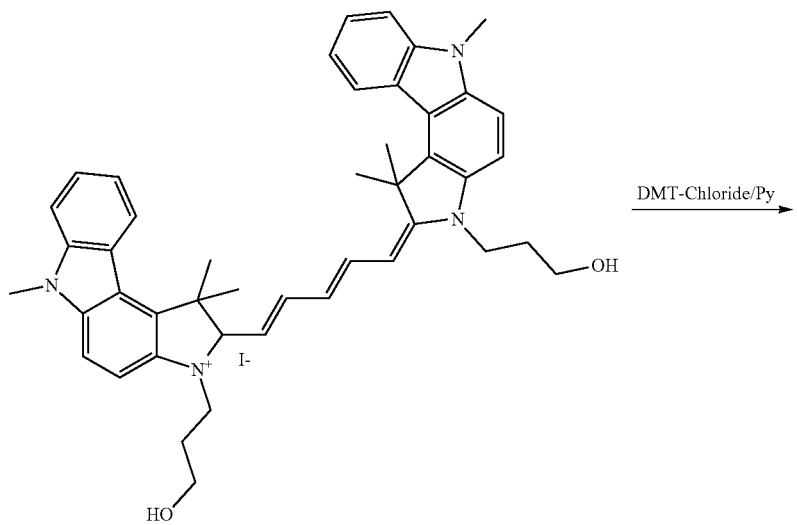

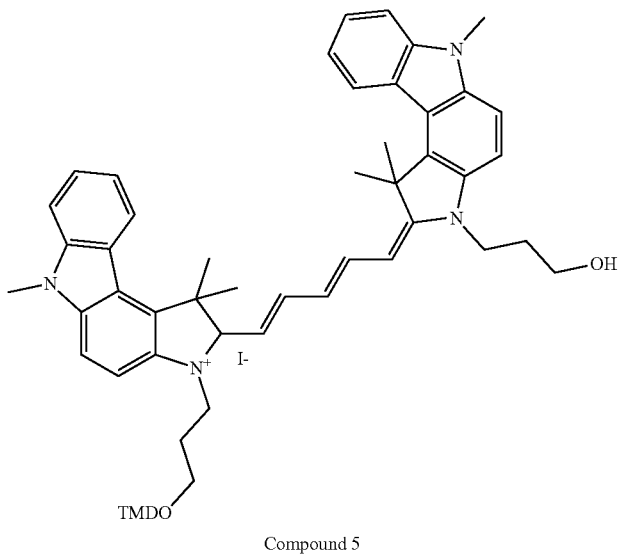

Compound 5

Synthesis of Intermediate 3

19.0 g (96.8 mmol) of 9-methyl-9-H-carbazole-3-amine (1; WO2002-096902), 16.1 g (116 mmol) of potassium carbonate, and 190 mL of dimethylformamide were put into a reactor, and 19.2 g (116 mmol) of 3-bromo-3-methylbutan-2-one (2; Organic Letters, 3(16), 2591-2594; 2001) was added thereto and stirred at 45° C. for 16 hours. The resulting mixture was concentrated under reduced pressure, then extracted with ethyl acetate and water, dried with magnesium sulfate, and filtered, and the filtrate was concentrated under reduced pressure. The concentrated substance was dissolved using 80 mL of dimethylformamide and 80 mL of toluene, and 6.8 g (57.1 mmol) of p-toluenesulfonic acid monohydrate was then added thereto. The resulting mixture was stirred at 120° C. for 16 hours, cooled to room temperature, and then concentrated under reduced pressure. The concentrated substance was extracted with ethyl acetate and water, dried with magnesium sulfate, and then filtered, and the filtrate was concentrated under reduced pressure and purified by silica gel column chromatography to obtain Intermediate 3 (12.0 g, 48%).

$^1$H NMR (300 MHz, CDCl$_3$): δ, 8.30 (d, J=8.1 Hz, 1H), 7.73 (d, J=8.4 Hz, 1H), 7.55-7.44 (m, 2H), 7.36 (d, J=8.4 Hz, 1H), 7.28 (dt, J1=6 Hz, J2=1.2 Hz, 1H), 3.90 (s, 3H), 2.37 (s, 3H), 1.69 (s, 6H).

Synthesis of Intermediate 5

Intermediate 3 (9.0 g, 34.3 mmol), Intermediate 4 (Organic Letters, 3(16), 2591-2594; 2001) (11.7 g, 51.5 mmol), and 90 mL of acetonitrile were put into a reactor and then stirred under reflux for 16 hours. The resulting mixture was cooled to room temperature, concentrated under reduced pressure, and then recrystallized to obtain Intermediate 5 (11 g, 65% yield).

$^1$H NMR (300 MHz, DMSO): δ, 8.40 (d, J=8.1 Hz, 1H), 8.1 (d, J=9.0 Hz, 1H), 7.92 (d, J=9.0 Hz, 1H), 7.79 (d, J=8.1 Hz, 1H), 7.66 (t, J=7.2 Hz, 1H), 7.40 (t, J=7.2 Hz, 1H), 4.65 (t, J=7.2 Hz, 2H), 4.20 (t, J=6.0 Hz, 2H), 4.00 (s, 3H), 2.91 (s, 3H), 2.30 (t, J=6.9 Hz, 2H), 1.92 (s, 3H), 1.84 (s, 6H).

Synthesis of Intermediate 7

Intermediate 5 (6.0 g, 12.2 mmol), Intermediate 6 (1.6 g, 6.11 mmol), and 40 mL of acetonitrile were put into a reactor, and 4.2 mL (30.6 mmol) of triethylamine and 1.2 mL (12.2 mmol) of acetic anhydride were added thereto and then stirred under reflux for 2 hours. The resulting mixture was cooled to room temperature and concentrated under reduced pressure, and then 2 N hydrochloric acid:methanol (1:1, 150 mL) was added thereto and stirred at room temperature for 16 hours. The resulting mixture was concentrated under reduced pressure, and an organic layer was then extracted with methylene chloride and water. The extracted organic layer was dried with sodium sulfate and purified by silica gel column chromatography to obtain Intermediate 7 (2.8 g, 56%).

$^1$H NMR (300 MHz, CDCl$_3$): δ 8.32 (d, J=8.1 Hz, 2H), 7.93 (t, J=12.6 Hz, 2H), 7.61-7.56 (m, 2H), 7.51-7.42 (m, 6H), 7.35 (t, J=7.5 Hz, 2H), 6.93 (t, J=5.4 Hz, 1H), 6.48 (d, J=13.8 Hz, 2H), 4.39 (t, J=6.6 Hz, 4H), 3.92 (brt, 4H), 3.90 (s, 6H), 2.18 (brt, 4H), 2.07 (s, 12H).

Synthesis of Compound 5

Intermediate 7 (2.8 g, 3.48 mmol), 30 mL of pyridine, and 4,4'-dimethoxytrityl chloride (1.3 g, 3.82 mmol) were put into a reactor. After the termination of a reaction was confirmed through TLC, methanol was added thereto, and the resulting mixture was concentrated under reduced pressure and purified by silica gel column chromatography to obtain Compound 5 (1.8 g, 46%).

$^1$H NMR (300 MHz, CDCl$_3$): δ 8.37-8.30 (m, 2H), 8.02-7.94 (m, 2H), 7.62-7.55 (m, 2H), 7.21-7.43 (m, 6H), 7.38-7.26 (m, 12H), 6.86-6.77 (m, 4H), 6.34 (brt, 1H), 6.20 (d, J=13.2 Hz, 2H), 4.51 (brt, 2H), 4.38-4.30 (m, 2H), 3.92 (brt, 2H), 3.91 (s, 6H), 3.82 (s, 6H), 3.21 (brt, 2H), 2.22-2.19 (m, 4H), 2.06 (s, 12H).

Preparation Example 2. Synthesis of Compound 6

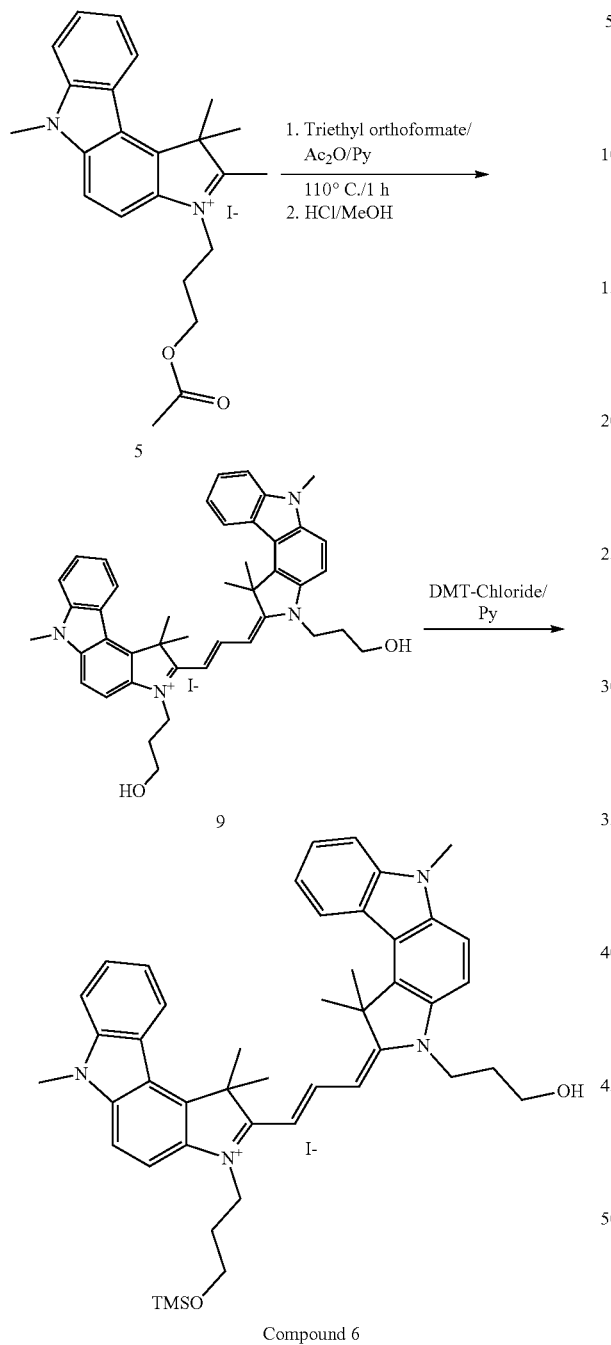

Synthesis of Intermediate 9

Triethyl orthoformate (0.97 g, 9.17 mmol), Intermediate 5 (9.0 g, 18.35 mmol) synthesized in Preparation Example 1, 40 mL of acetic anhydride, and 10 mL of pyridine were put into a reactor and then stirred at 110° C. for 2 hours. The mixture was concentrated under reduced pressure, and 180 mL of methanol and 30 mL of concentrated hydrochloric acid were added thereto and stirred at room temperature for 16 hours. The resulting mixture was concentrated under reduced pressure and then extracted with methylene chloride and water. The extracted substance was dried with sodium sulfate and filtered, and the filtrate was then concentrated under reduced pressure and purified by silica gel column chromatography to obtain Intermediate 9 (5.0 g, 63%).

$^1$H NMR (300 MHz, CDCl$_3$): δ 8.54 (t, J=13.5 Hz, 1H), 8.38-8.29 (m, 3H), 7.64-7.59 (m, 2H), 7.53-7.50 (m, 2H), 7.47-7.42 (m, 2H), 7.41-7.27 (m, 4H), 6.99 (d, J=13.5 Hz, 2H), 4.45 (t, J=6.6 Hz, 4H), 3.99 (t, J=5.4 Hz, 4H), 3.92 (s, 6H), 2.26 (brt, 4H), 2.16 (s, 12H).

Synthesis of Compound 6

Intermediate 9 was used instead of Intermediate 7 of Preparation Example 1 to obtain Compound 6 (42%).

$^1$H NMR (300 MHz, CDCl$_3$): δ, 8.49 (t, J=13.5 Hz, 1H), 8.36 (m, J=7.8 Hz, 2H), 7.64-7.59 (m, 2H), 7.55-7.50 (m, 2H), 7.47-7.20 (m, 15H), 6.99-6.92 (m, 2H), 6.76-6.73 (d, J=9 Hz, 4H), 4.50 (t, J=6.6 Hz, 2H), 4.43 (t, J=6.3 Hz, 2H), 3.97 (brt, 2H), 3.93 (s, 3H), 3.92 (s, 3H), 3.72 (s, 6H), 3.27 (t, J=5.1 Hz, 2H), 2.36 (brt, 2H), 2.33 (brt, 2H), 2.15 (s, 6H), 2.07 (s, 6H).

Preparation Example 3. Synthesis of Compound 7

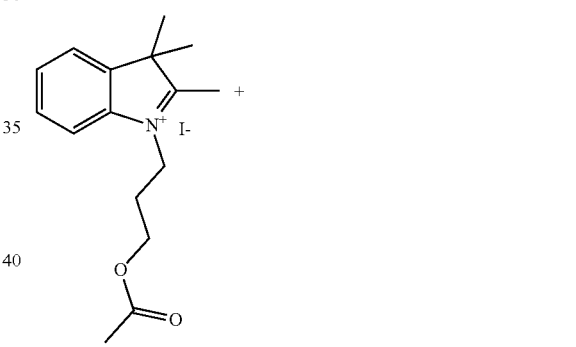

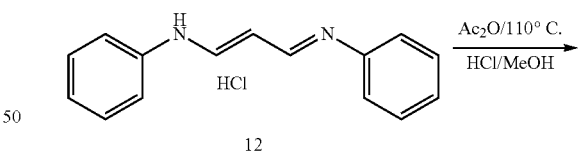

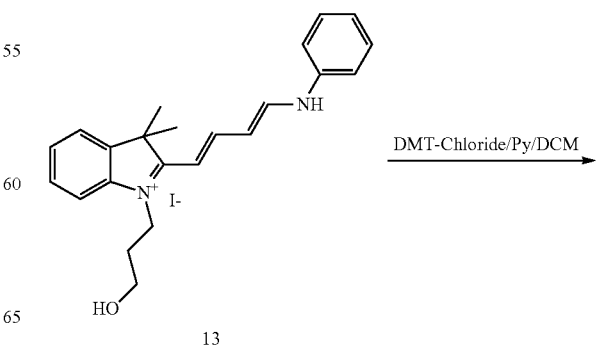

23

-continued

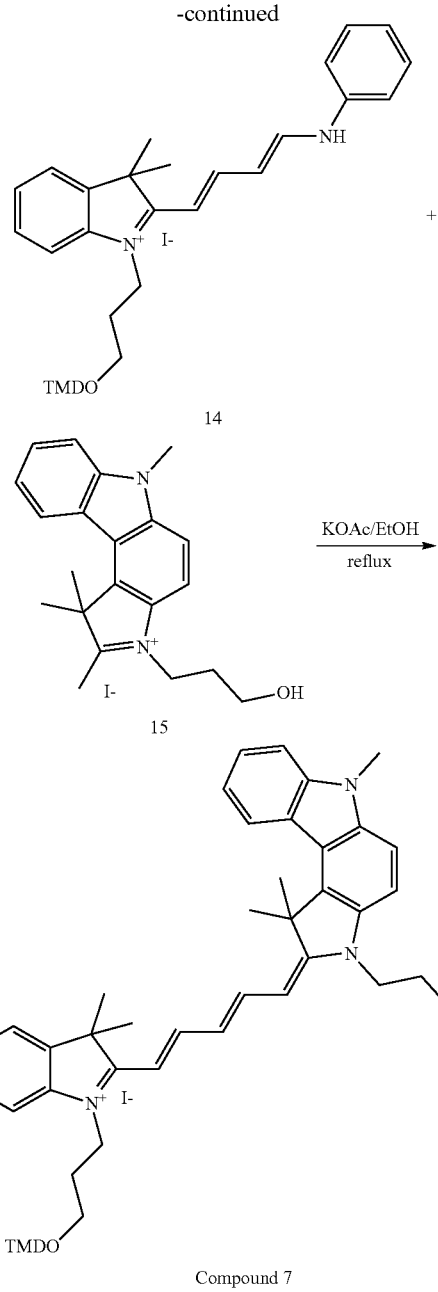

Synthesis of Intermediate 13

Intermediate 11 (US005556959A) (8.0 g, 20.7 mmol), Intermediate 12 (6.4 g, 24.8 mmol), and 80 mL of acetic anhydride were put into a reactor, then stirred at 110° C. for 2 hours, and concentrated under reduced pressure. Afterward, 350 mL of methanol and 60 mL of concentrated hydrochloric acid were added thereto and stirred at room temperature for 16 hours. The resulting solution was concentrated under reduced pressure and then extracted with methylene chloride and water. The extracted substance was dried with sodium sulfate and filtered, and the filtrate was then concentrated under reduced pressure and purified by silica gel column chromatography to obtain Intermediate 13 (4.8 g, 24.8 mmol).

24

$^1$H NMR (300 MHz, CDCl$_3$): δ 8.53 (d, J=11.7 Hz, 1H), 8.20 (t, J=12.9 Hz, 1H), 7.61 (d, J=8.1 Hz, 2H), 7.40-7.31 (m, 4H), 7.23-7.20 (m, 2H), 7.13 (t, J=7.5 Hz, 1H), 7.04 (d, J=12.3 Hz, 1H), 6.26 (d, J=13.8 Hz, 1H), 4.17 (t, J=7.2 Hz, 2H), 3.83 (t, J=5.1 Hz, 2H), 2.05 (brt, 2H), 1.71 (s, 6H).

Synthesis of Intermediate 14

Intermediate 13 was used instead of Intermediate 7 of Preparation Example 1 to obtain Intermediate 14 (2.7 g, 42%).

$^1$H NMR (300 MHz, CDCl$_3$): δ 8.31 (d, J=9.6 Hz, 1H), 7.96 (t, J=12.9 Hz, 1H), 7.43-7.06 (m, 20H), 6.83 (d, J=9.0 Hz, 4H), 5.89 (d, J=13.5 Hz, 1H), 4.04 (brt, 2H), 3.81 (s, 6H), 3.21 (t, J=5.4 Hz, 2H), 2.05 (brt, 2H), 1.63 (s, 6H).

Synthesis of Intermediate 15

3-Iodopropanol was used instead of Intermediate 4 of Preparation Example 1 to obtain Intermediate 15 (52%).

$^1$H NMR (300 MHz, DMSO): δ, 8.39 (d, J=8.4 Hz, 1H), 8.07 (d, J=8.7 Hz, 1H), 7.91 (d, J=8.7 Hz, 1H), 7.78 (d, J=8.4 Hz, 1H), 7.64 (t, J=7.2 Hz, 1H), 7.39 (t, J=7.5 Hz, 1H), 4.63 (t, J=6.9 Hz, 2H), 4.00 (s, 3H), 3.58 (t, J=5.4 Hz, 2H), 2.89 (s, 3H), 2.10 (brt, 2H), 1.82 (s, 6H).

Synthesis of Compound 7

Intermediate 14 (1.9 g, 2.45 mmol), Intermediate 15 (1.1 g, 2.45 mmol), 0.29 g (2.94 mmol) of potassium acetate, and 30 mL of ethanol were put into a reactor and stirred under reflux for 16 hours. The resulting mixture was cooled to room temperature, then concentrated under reduced pressure, and purified by silica gel column chromatography to obtain Compound 7 (1.2 g, 49%).

$^1$H NMR (300 MHz, CDCl$_3$): δ 8.32 (d, J=7.5 Hz, 1H), 8.03 (t, J=14.1 Hz, 1H), 7.85 (t, J=12.6 Hz, 1H), 7.60 (t, J=8.7 Hz, 2H), 7.51 (d, J=8.7 Hz, 2H), 7.45 (d, J=7.2 Hz, 2H), 7.35-7.21 (m, 9H), 7.13 (d, J=7.5 Hz, 1H), 6.99 (d, J=7.5 Hz, 1H), 6.84 (d, J=9.0 Hz, 4H), 6.50 (d, J=13.2 Hz, 1H), 6.43 (brt, 1H), 6.04 (d, J=13.5 Hz, 1H), 4.59 (t, J=7.2 Hz, 2H), 4.10 (brt, 4H), 3.95 (s, 6H), 3.82 (s, 6H), 3.15 (t, J=5.1 Hz, 2H), 2.23 (brt, 4H), 2.06 (s, 6H), 1.67 (s, 6H).

Preparation Example 4. Synthesis of Compound 8

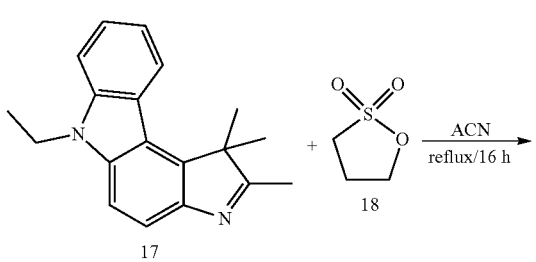

25
-continued

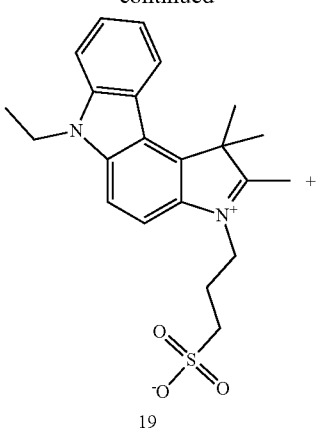

19

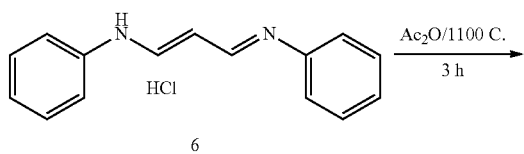

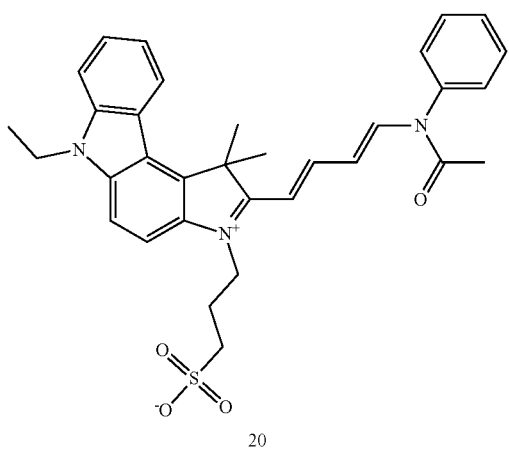

20

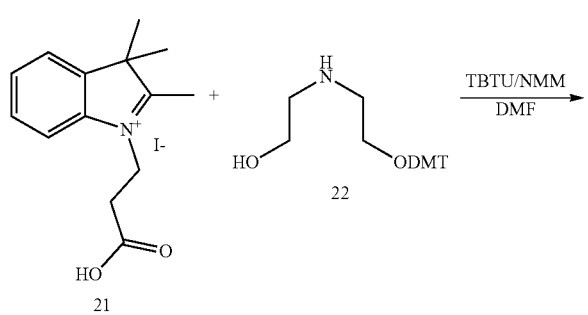

26
-continued

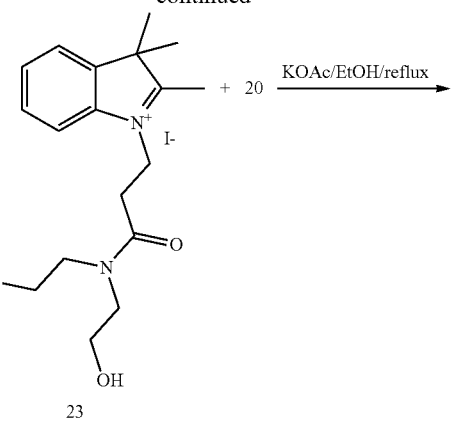

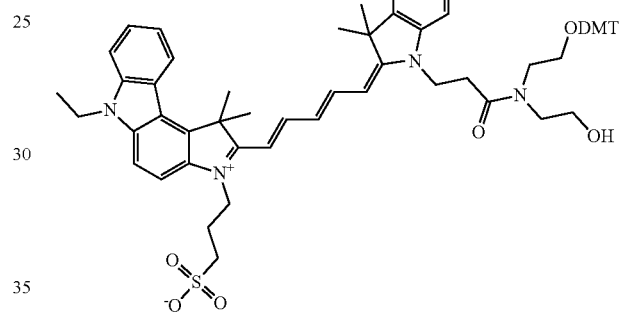

Compound 8

Synthesis of Intermediate 17

3-Amino-9-ethylcarbazole was used instead of Intermediate 1 of Preparation Example 1 to obtain Intermediate 17 (52%).

$^1$H NMR (300 MHz, CDCl$_3$): δ 8.31 (d, J=7.8 Hz, 1H), 7.72 (d, J=8.4 Hz, 1H), 7.54-7.45 (m, 2H), 7.37 (d, J=8.4 Hz, 1H), 7.28 (dt, J1=6 Hz, J2=1.5 Hz, 1H), 4.41 (q, 2H), 2.37 (s, 3H), 1.69 (s, 6H), 1.47 (t, J=7.2 Hz, 3H).

Synthesis of Intermediate 19

Intermediate 17 (8 g, 28.95 mmol), Intermediate 18 (7.1 g, 57.8 mmol), and 80 mL of acetonitrile were put into a reactor and stirred under reflux for 16 hours. The precipitated solid was filtered, washed with heptane, and then dried under reduced pressure to obtain Intermediate 19 (8.8 g, 75%).

$^1$H NMR (300 MHz, DMSO): δ, 8.36 (d, J=8.1 Hz, 1H), 8.18 (d, J=9.0 Hz, 1H), 7.94 (d, J=9.0 Hz, 1H), 7.78 (d, J=8.4 Hz, 1H), 7.62 (t, J=7.2 Hz, 1H), 7.38 (t, J=7.8 Hz, 1H), 4.76 (t, J=7.5 Hz, 2H), 4.58 (q, 2H), 2.89 (s, 3H), 2.67 (t, J=6.3 Hz, 2H), 2.25 (q, 2H), 1.82 (s, 6H), 1.33 (t, J=6.9 Hz, 3H).

Synthesis of Intermediate 20

Intermediate 19 (5 g, 12.6 mmol), Intermediate 6 (3.6 g, 13.8 mmol), and 50 mL of acetic anhydride were put into a reactor and then stirred at 110° C. for 2 hours. The resulting mixture was cooled to room temperature and purified by silica gel column chromatography to obtain Intermediate 20 (5.7 g, 77%).

Synthesis of Intermediate 23

Intermediate 21 (Journal of Medicinal Chemistry, 59(5), 2151-2162; 2016) (3.5 g, 9.74 mmol), Intermediate 22 (Journal of the American Chemical Society, 2004, 126 (27), 8364-8365) (4 g, 9.74 mmol), 1-[bis(dimethylamino)methylene]-1H-benzotriazolium 3-oxide tetrafluoroborate (4.8 g, 15.0 mmol), 40 mL of dimethylformamide, and triethylamine (4.16 mL, 30 mmol) were put into a reactor and then stirred at room temperature for 3 hours. The reaction solution was poured into ice water, and then the precipitated solid was filtered, washed with water, dried under reduced pressure, and purified by silica gel column chromatography to obtain Intermediate 23 (4.2 g, 56%).

Synthesis of Compound 8

Intermediate 23 was used instead of Intermediate 15 of Preparation Example 3, and Intermediate 20 was used instead of Intermediate 14 of Preparation Example 3 to obtain Compound 8 (74%).

Preparation Example 5. Synthesis of Compound 9

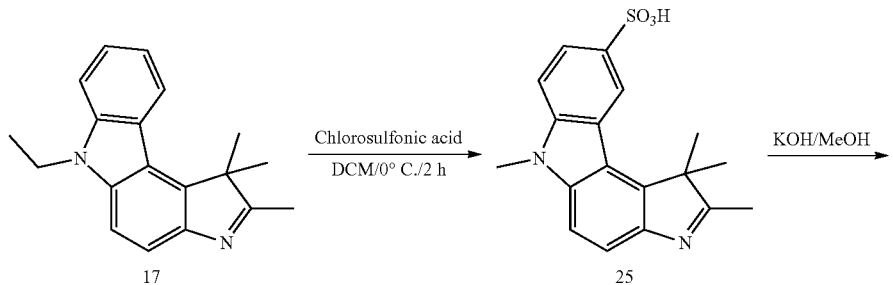

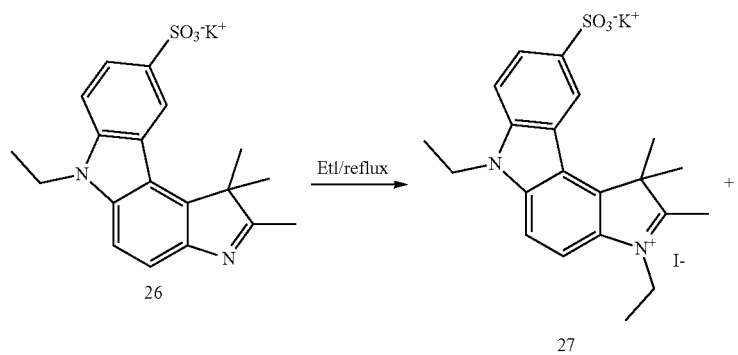

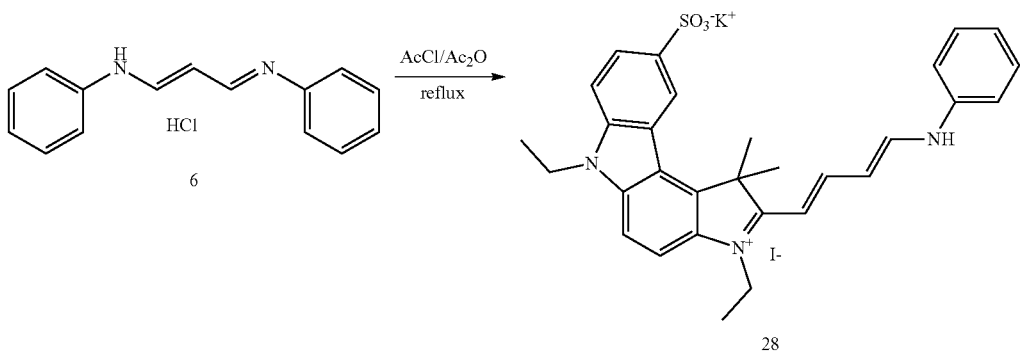

-continued
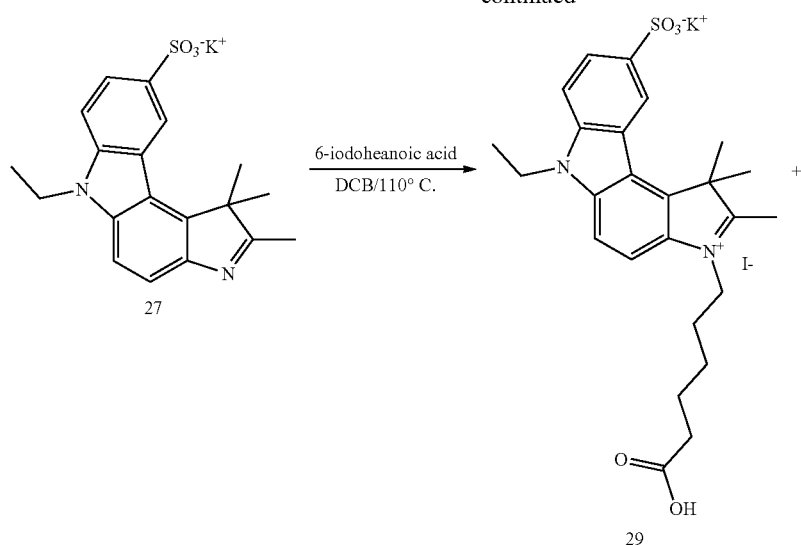
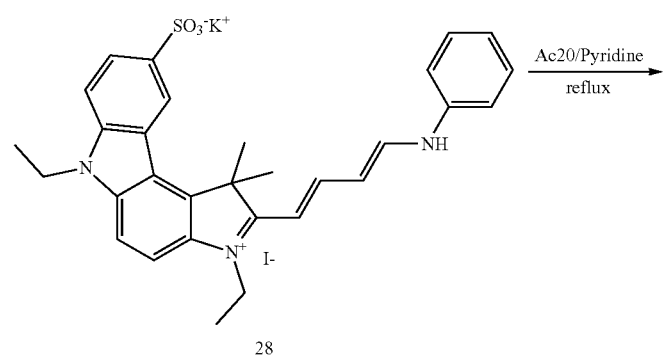
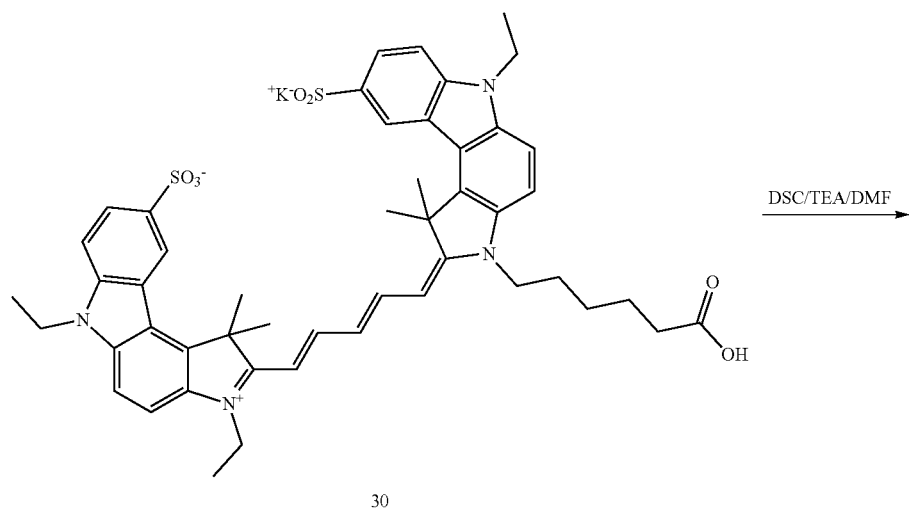

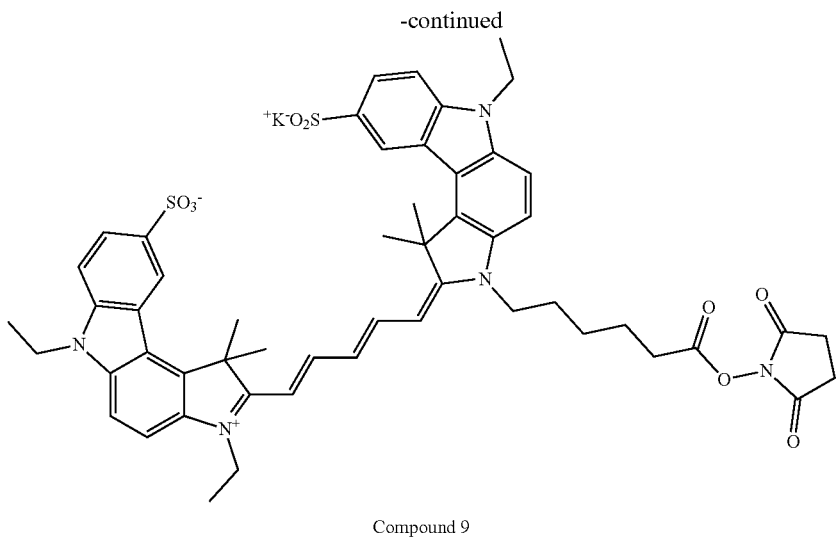

Compound 9

Synthesis of Intermediate 25

Intermediate 17 (5 g, 18.09 mmol), chlorosulfonic acid (2.6 ml, 39.80 mmol), and dichloromethane (100 mL) were put into a 250-mL one-neck reactor and stirred at room temperature for 2 hours. A solid was precipitated with ethyl acetate (500 mL), filtered, and dried.

$^1$H NMR (300 MHz, DMSO): δ 8.58 (s, 1H), 7.87-7.71 (m, 4H), 4.55 (q, 2H), 2.77 (s, 3H), 1.81 (s, 6H), 1.32 (t, J=6.9 Hz, 3H).

Synthesis of Intermediate 26

Intermediate 25 (6.1 g, 17.11 mmol), potassium hydroxide (2.72 g, 51.34 mmol), and methanol (60 mL) were put into a 250-mL one-neck reactor and stirred under reflux for an hour. The resulting mixture was cooled, and a solid was precipitated with diethyl ether, filtered, and dried.

$^1$H NMR (300 MHz, D20): δ 8.28 (s, 1H), 7.67 (d, J=8.7 Hz, 1H), 7.15 (d, J=9.0 Hz, 1H), 7.7.01 (d, J=8.4 Hz, 1H), 6.63 (d, J=8.7 Hz, 1H), 3.63 (q, 2H), 2.01 (s, 3H), 1.03 (s, 6H), 0.74 (t, J=6.9 Hz, 3H).

Synthesis of Intermediate 27

Intermediate 26 (3.0 g, 7.60 mmol) and ethyl iodide (30 mL) were put into a 250-mL one-neck reactor and stirred under reflux for 16 hours. The resulting mixture was concentrated, and a solid was precipitated with diethyl ether, filtered, and dried.

$^1$H NMR (300 MHz, DMSO): δ 8.60 (s, 1H), 8.10 (d, J=9.0 Hz, 1H), 7.95 (d, J=8.7 Hz, 1H), 7.87 (d, J=8.7 Hz, 1H), 7.73 (d, J=8.4 Hz, 1H), 4.59 (q, 4H), 2.89 (s, 3H), 1.83 (s, 6H), 1.51 (t, J=6.9 Hz, 3H), 1.32 (t, J=6.6 Hz, 3H).

Synthesis of Intermediate 28

Intermediate 27 (2 g, 3.63 mmol), malonaldehyde dianilide hydrochloride (1.13 g, 4.36 mmol), acetic acid (5 mL), and acetic anhydride (20 mL) were put into a 100-mL one-neck reactor and stirred at 100° C. for an hour. Subsequently, a solid was precipitated with ethyl acetate, filtered, and dried.

Synthesis of Intermediate 29

Intermediate 26 (3.0 g, 7.60 mmol), 6-iodohexanoic acid (2.76 g, 11.41 mmol), and 1,2-dichlorobenzene (30 mL) were put into a 100-mL one-neck reactor and stirred at 110° C. for 16 hours. Subsequently, a solid was precipitated with ethyl acetate, filtered, and dried.

$^1$H NMR (300 MHz, DMSO): δ, 8.60 (s, 1H), 8.10 (d, J=9.0 Hz, 1H), 7.93 (d, J=9.0 Hz, 1H), 7.87 (d, J=8.7 Hz, 1H), 7.73 (d, J=8.7 Hz, 1H), 4.57 (m, 4H), 2.90 (s, 3H), 2.24 (t, J=7.2 Hz, 2H), 1.91 (br s, 2H), 1.83 (s, 6H), 1.57 (m, 5H), 1.32 (m, 5H).

Synthesis of Intermediate 30

Intermediate 28 (2.2 g, 3.24 mmol), Intermediate 29 (2.06 g, 3.24 mmol), acetic anhydride (0.9 ml, 9.71 mmol), and pyridine (40 mL) were put into a 100-mL one-neck reactor and stirred under reflux for 2 hours. Subsequently, the resulting mixture was concentrated and then purified by reversed-phase chromatography.

$^1$H NMR (300 MHz, DMSO): δ, 8.88 (s, 2H), 8.25 (t, J=13.5 Hz, 2H), 8.07 (dd, 2H), 7.68-7.60 (m, 4H), 7.54-7.50 (m, 2H), 6.63 (t, J=12.6 Hz, 1H), 6.24 (d, J=14.4 Hz, 1H), 4.48 (m, 4H), 4.25 (m, 4H), 2.36 (t, J=6.9 Hz, 2H), 2.03 (d, 12H), 1.92 (m, 2H), 1.72 (m, 2H), 1.60 (m, 2H), 1.41-1.37 (m, 9H).

Synthesis of Compound 9

Intermediate 30 (0.14 g, 0.15 mmol), N,N'-disuccinimidyl carbonate (0.116 g, 0.45 mmol), triethylamine (0.06 ml, 0.45 mmol), and N,N'-dimethylformamide (3 mL) were put into a 100-mL one-neck reactor and stirred at room temperature for 16 hours. Subsequently, a solid was precipitated with ethyl acetate, filtered, and dried.

$^1$H NMR (300 MHz, DMSO): δ, 8.74 (s, 2H), 8.53 (t, J=13.2 Hz, 2H), 7.85 (d, J=9.3 Hz 2H), 7.75-7.71 (m, 2H), 7.67-7.58 (m, 4H), 6.55 (t, J=12.6 Hz, 1H), 6.28 (d, J=13.8 Hz, 1H), 4.53 (m, 4H), 4.25 (m, 4H), 2.81 (s, 4H), 2.2.71 (t, J=6.9 Hz, 2H), 2.08 (d, 12H), 1.81 (m, 2H), 1.73 (m, 2H), 1.54 (m, 2H), 1.38-1.31 (m, 9H).

Preparation Example 6. Synthesis of Quencher-CPG

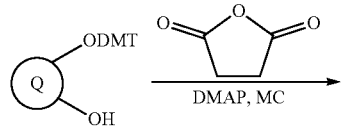

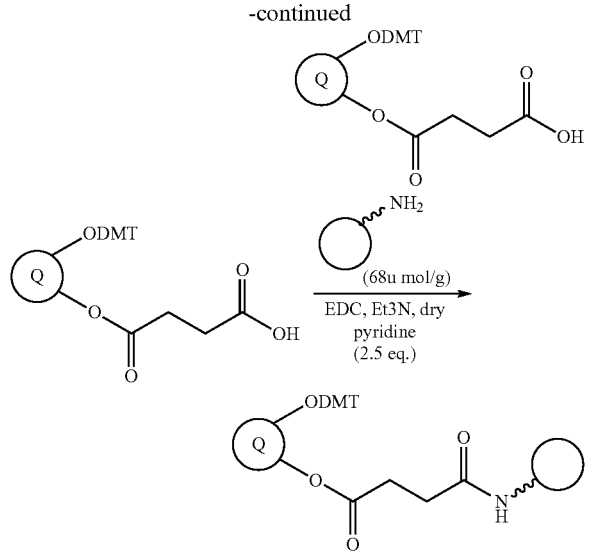

Compound 5 (75 mg, 0.11 mmol), succinic anhydride (9.9 mg, 0.099 mmol), 4-dimethylaminopyridine (12.1 mg, 0.099 mmol), and dichloromethane (5 ml) were put into a 10 mL vial and rolled at room temperature for 1.5 hours. The resulting mixture was completely concentrated, and 1-ethyl-3-(3-dimethylaminopropyl)carbodiimide (52.7 mg, 0.275 mmol), triethylamine (28 ul), pyridine (5 ml), and CPG-NH$_2$ (1 g) were added thereto and rolled at room temperature for 2 hours. The powder was filtered and washed three times each with acetonitrile, methanol, and dichloromethane. The resulting powder was dried, and CapA/CapB=1 ml/1 ml was added to the powder, then rolled at room temperature for 2 hours, washed three times each with acetonitrile and dichloromethane, and dried.

Preparation Example 7. Synthesis of Single-Labeled Oligonucleotide

A single-labeled oligonucleotide was synthesized using Compound 5-CPG through a 10-Column Polygen DNA Synthesizer. The sequence of the single-labeled oligonucleotide thus synthesized is shown in Table 1 below.

TABLE 1

| Classification | Sequence |
|---|---|
| Compound 5-SEQ ID No. 1 (T10) | 3'-Compound 5-TTT TTT TTT T-5' |
| Compound 5-SEQ ID No. 2 (T12) | 3'-Compound 5-TTT TTT TTT TTT-5' |
| Compound 5-SEQ ID No. 3 (T14) | 3'-Compound 5-TTT TTT TTT TTT TT-5' |
| Compound 5-SEQ ID No. 4 (T16) | 3'-Compound 5-TTT TTT TTT TTT TTT T-5' |
| Compound 5-SEQ ID No. 5 (T18) | 3'-Compound 5-TTT TTT TTT TTT TTT TTT-5' |
| Compound 5-SEQ ID No. 6 (T20) | 3'-Compound 5-TTT TTT TTT TTT TTT TTT TT-5' |

Figure 2:
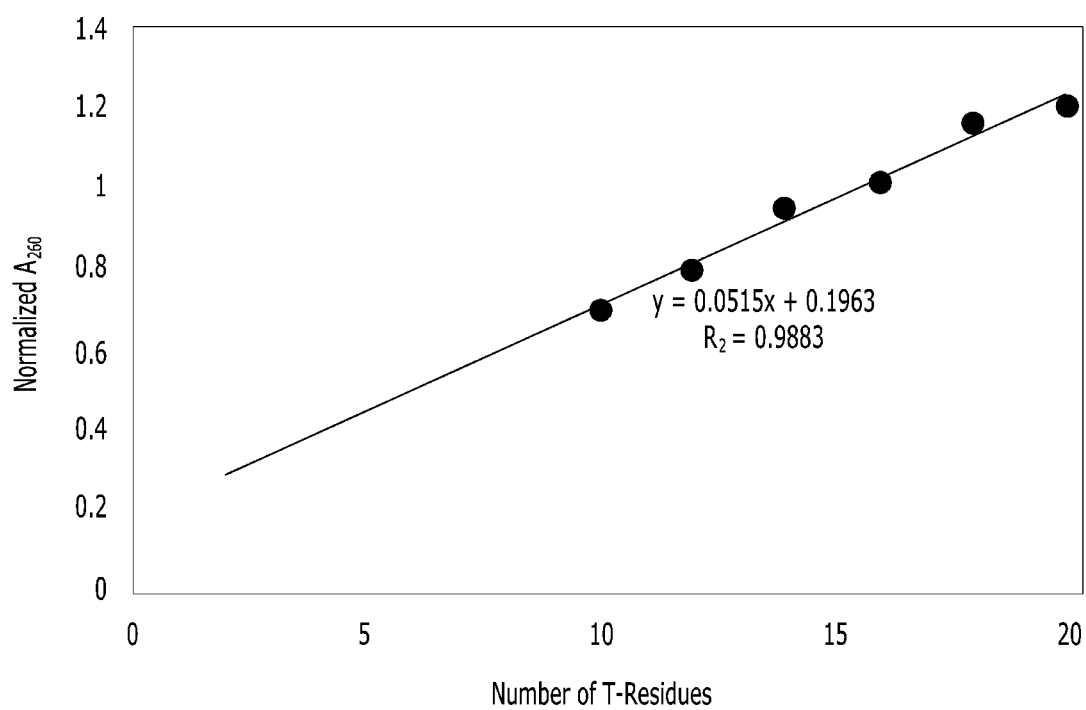
FIG. 2 shows an absorbance at 260 nm in FIG. 1.

After being synthesized, the single-labeled oligonucleotide was deprotected by a common method and purified by RP-HPLC. The absorption spectrum of the synthesized single-labeled oligonucleotide after purification is shown in FIG. 1. In addition, an absorption coefficient at 260 nm in the absorption spectrum of FIG. 1 was measured (see FIG. 2), and a measured value was 30,274.

Preparation Example 8. Synthesis of Dual-Labeled Oligonucleotide

A dual-labeled oligonucleotide was synthesized using Compound 5-CPG and Cy5-phosphoramidite (Glen Research) through a 10-Column Polygen DNA Synthesizer. The sequence of the dual-labeled oligonucleotide thus synthesized is shown in Table 2 below.

TABLE 2

| Classification | Sequence |
|---|---|
| Compound 5-SEQ ID No. 7 (b Actin)-Cy5 | 3'-Compound 5-ATG CCC TCC CCC ATG CCA TCC TGC GT-Cy5-5' |

Experimental Examples. Measurement of Quenching Characteristics of Quencher

Experimental Example 1

The $\lambda_{abs, Max}$ (nm) and absorption coefficient (e) of Compound 5 prepared according to Preparation Example 1 were confirmed. The results thereof are shown in Table 3 below.

TABLE 3

| Classification | $\lambda_{abs, Max}$ (nm) | Absorption coefficient (e) |
| --- | --- | --- |
| Compound 5 | 650 | 21,000 |

Referring to the results of Table 3, it can be seen that the quencher according to the present invention exhibited absorption characteristics at a wavelength range of 590 nm or more, and accordingly, it is possible to design a dual-labeled probe by using the quencher in combination with a variety of fluorophores.

Figure 3:
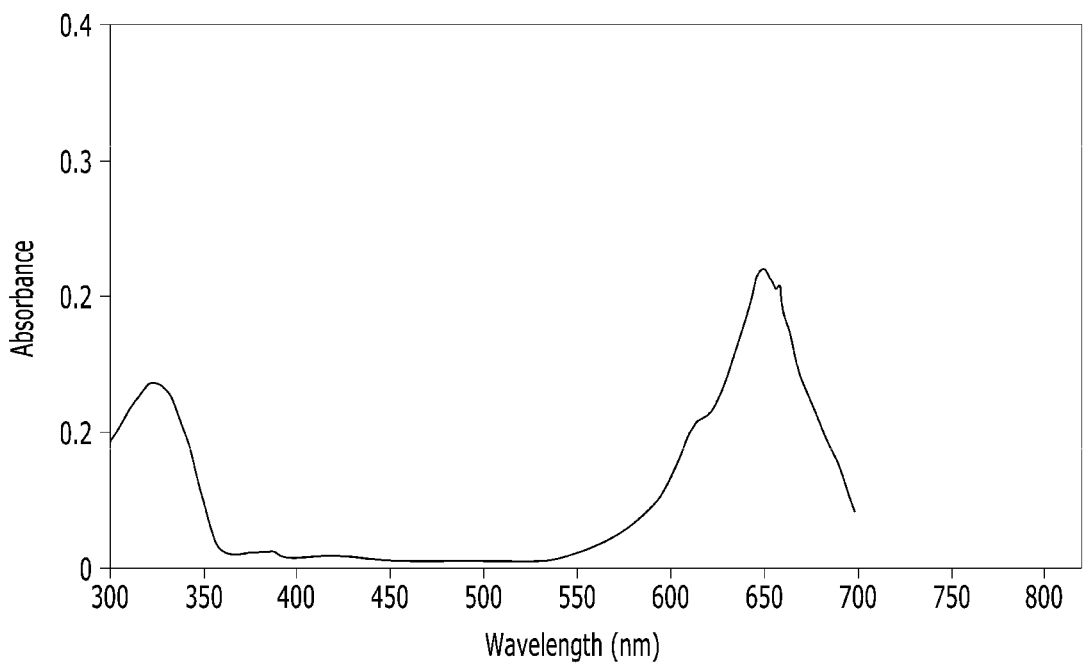
FIG. 3 shows an absorption spectrum of a quencher according to another embodiment of the present invention.

In addition, referring to FIG. 3 that shows the absorption spectrum of Compound 7 prepared according to Preparation Example 3, it can be seen that the quencher according to Compound 7 also exhibited absorption characteristics at a wavelength range of 590 nm.

Experimental Example 2

Figure 4:
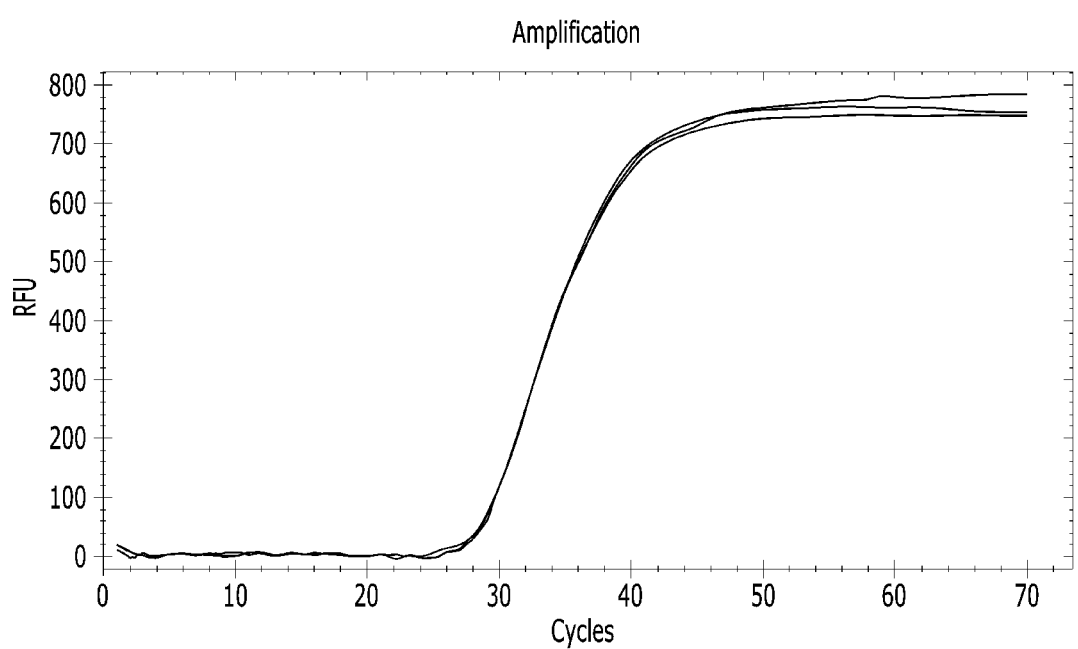
FIG. 4 shows a result of real-time PCR amplification using a dual-labeled probe including a quencher according to an embodiment of the present invention.

In order to confirm the quenching characteristics of a dual-labeled probe, a dual-labeled probe was designed as shown in Table 4 below. Subsequently, real time PCR was performed using the composition described in Table 5 below (using Bio-Rad CFX-96), and the results thereof are shown in FIG. 4.

TABLE 4

| 5' Fluorophore | Probe sequence (SEQ ID No. 8) | 3' Quencher |
| --- | --- | --- |
| Cy5 | ATG CCC TCC CCC ATG CCA TCC TGC GT | Compound 5 |

TABLE 5

| Classification | Content (µl) |
| --- | --- |
| (Enzynomics)TOPreal ™ qPCR 2X Pre-MIX (TaqMan Probe) | 10 |
| gDNA (10 ng/µl) | 1 |
| Beta-actin F/R MIX (5 pmole/µl) | 1 |
| B-actin probe (3 pmole/µl) | 3 |
| DEPC water | 5 |

Referring to FIG. 3 that shows the real time PCR result of a dual-labeled probe composed of Cy5 and Compound 5 as a fluorophore and a quencher, respectively, it can be seen that Compound 5 effectively quenched the fluorescence of Cy5, and PCR amplification also proceeded in an ideal pattern.

Experimental Example 3

Figure 5:
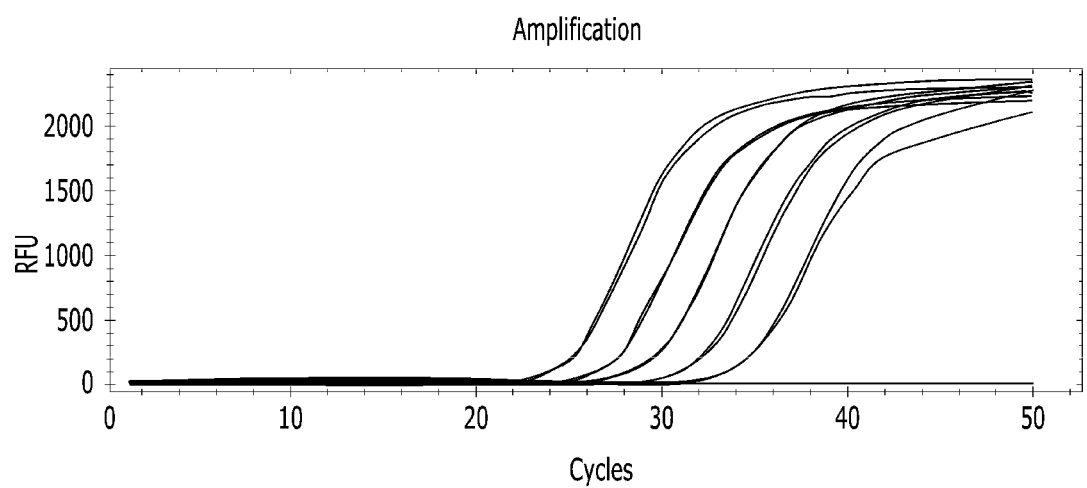
FIG. 5 shows a result of real-time PCR amplification using a dual-labeled probe including a quencher according to another embodiment of the present invention.

In order to confirm the quenching characteristics of a dual-labeled probe synthesized using Compound 7, a dual-labeled probe was designed as shown in Table 6 below. Subsequently, real time PCR was performed using the composition described in Table 7 below (using Bio-Rad CFX-96), and the results thereof are shown in FIG. 5.

TABLE 6

| 5' Fluorophore | Probe sequence (SEQ ID No. 9) | 3' Quencher |
| --- | --- | --- |
| Cy5 | TCA GCA AAT GCA TCA CAA ACA GAT AAT GGC | Compound 7 |

TABLE 7

| Classification | Content |
| --- | --- |
| Master Mix (Biolin Probe Master Mix (2X)) | 20 µl |
| Primer | 10 pmole each |
| Cy5-Compound 7 probe | 5 pmole |
| Template | Hyman gDNA 1 ng & Staphylococcus aureus gDNA 200 pg, 40 pg, 8 pg, 1.6 pg, 032 pg |
| PCR water | up to 40 µl |

Referring to FIG. 5 that shows the real time PCR result of a dual-labeled probe composed of Cy5 and Compound 7 as a fluorophore and a quencher, respectively, it can be seen that Compound 7 effectively quenched the fluorescence of Cy5, and PCR amplification also proceeded in an ideal pattern.

Experimental Example 4

Figure 6:
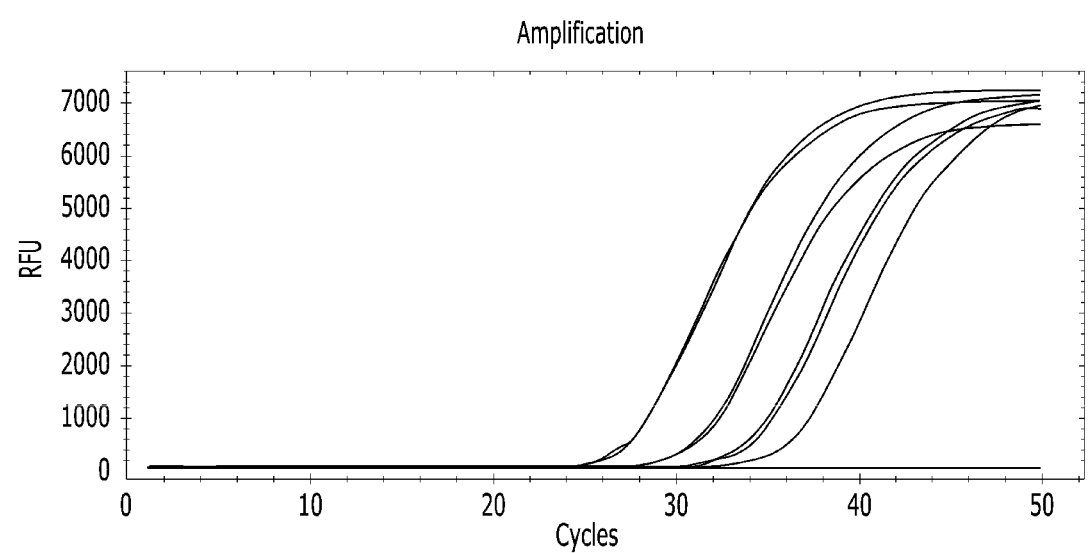
FIG. 6 shows a result of real-time PCR amplification using a dual-labeled probe including a quencher according to still another embodiment of the present invention.

In order to confirm the quenching characteristics of a dual-labeled probe synthesized using Compound 9, a dual-labeled probe was designed as shown in Table 8 below. Subsequently, real time PCR was performed using the composition described in Table 9 below (using Bio-Rad CFX-96), and the results thereof are shown in FIG. 6.

TABLE 8

| 5' Fluorophore | Probe sequence (SEQ ID No. 10) | 3' Quencher |
| --- | --- | --- |
| CalFluorRed 610 | TCA GCA AAT GCA TCA CAA ACA GAT AAT GGC | Compound 9 |

TABLE 9

| Classification | Content |
| --- | --- |
| Master Mix (Biolin Probe Master Mix (2X)) | 20 µl |
| Primer | 10 pmole each |
| CalFluorRed 610-Compound 9 probe | 4 pmole |
| Template | BQCV plasmid 1/5 dilution from $10^4$, 4 point |
| PCR water | up to 40 µl |

Referring to FIG. 6 that shows the real time PCR result of a dual-labeled probe composed of CalFluorRed 610 and Compound 9 as a fluorophore and a quencher, respectively, it can be seen that Compound 9 effectively quenched the fluorescence of CalFluorRed 610, and PCR amplification also proceeded in an ideal pattern.

The present invention relates to a quencher having a quenching effect on a fluorescent material exhibiting luminescence characteristics at an excited energy level, and various uses thereof. The quencher according to the present invention can exhibit excellent quenching characteristics as quenching efficiency is higher than that of a conventional quencher.

It will be apparent to a person who has an ordinary knowledge in the art that various modifications and corrections by addition, change or deletion of the constitutive components may be made without departing from the spirit of the invention as set forth in the appended claims. The above modifications and corrections are also within the scope of the present invention.

What is claimed is:

1. A quencher represented by Chemical Formula 1 below:

[Chemical Formula 1]

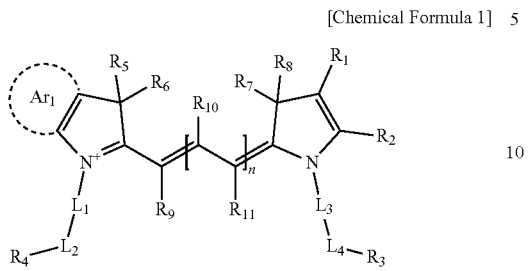

wherein $R_1$ and $R_2$ are bonded to a and b, b and c, or c and d of Chemical Formula 2 below, respectively,

[Chemical Formula 2]

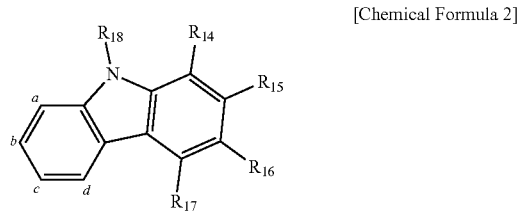

$Ar_1$ is selected from a substituted or unsubstituted aryl, a substituted or unsubstituted heteroaryl, and Chemical Formula 2, n is an integer of 1 to 3, $R_3$ to $R_{18}$ are each independently selected from: a functional group selected from hydrogen, deuterium, a substituted or unsubstituted $C_1$-$C_{10}$ alkyl, a substituted or unsubstituted $C_1$-$C_{10}$ heteroalkyl including at least one heteroatom, a substituted or unsubstituted $C_2$-$C_{10}$ alkenyl, a substituted or unsubstituted $C_2$-$C_{10}$ alkynyl, a substituted or unsubstituted $C_1$-$C_{10}$ alkoxy, a substituted or unsubstituted aryloxy, a substituted or unsubstituted $C_1$-$C_{10}$ haloalkyl, a halogen, a cyano, a hydroxy, a substituted or unsubstituted amino, a substituted or unsubstituted amide, a carbamate, a sulfhydryl, a nitro, a carboxyl, a carboxylate, a substituted or unsubstituted aryl, a substituted or unsubstituted heteroaryl, a substituted or unsubstituted aralkyl, quaternary ammonium, phosphoric acid, a phosphate, a substituted ketone, an aldehyde, a substituted ester, a substituted sulfonyl, a substituted or unsubstituted sulfonamide, an acyl chloride, a sulfonic acid, a sulfonate, hydrazine, a thiol, an acetal, a ketal, a phosphonate (a phosphite), a hypophosphite, sulfohydroxy, a sulfate, azido, guanidium, a ketene, a thiocarbonyl, an aminothiocarbonyl, a polyalkylene oxide, a carboxyl, a carboxyl derivative, a hydroxyl, a haloalkyl, a dienophile, an aldehyde, a ketone, a sulfonyl halide, a thiol, an amine, a sulfhydryl, an alkene, an epoxide, and a phosphoramidite; or a reactive group capable of covalently bonding to the functional group, $R_5$ and $R_6$ are each independently present or linked to each other to form a ring, $R_7$ and $R_8$ are each independently present or linked to each other to form a ring, $L_1$ and $L_3$ are single bonds or linkers including 1 to 40 non-hydrogen atoms, and $L_2$ and $L_4$ are linkers including 1 to 40 non-hydrogen atoms, and at least one substituent among $R_3$ to $R_{18}$ and $Ar_1$ is a functional group selected from a carboxyl, a carboxyl derivative, a hydroxyl, a haloalkyl, a dienophile, an aldehyde, a ketone, a sulfonyl halide, a thiol, an amine, a sulfhydryl, an alkene, an epoxide, and a phosphoramidite or a reactive group capable of covalently bonding to the functional group.

2. The quencher of claim 1, wherein $R_1$ and $R_2$ are bonded to a and b respectively.

3. The quencher of claim 1, wherein $R_1$ and $R_2$ are bonded to b and c respectively.

4. The quencher of claim 1, wherein $R_1$ and $R_2$ are bonded to c and d respectively.

5. The quencher of claim 1, wherein at least one of $R_3$ and $R_4$ is a functional group selected from a carboxyl, a carboxyl derivative, a hydroxyl, a haloalkyl, a dienophile, an aldehyde, a ketone, a sulfonyl halide, a thiol, an amine, a sulfhydryl, an alkene, an epoxide, and a phosphoramidite or a reactive group capable of covalently bonding to the functional group.

6. The quencher of claim 1, wherein the reactive group is selected from a carboxyl, a carboxyl derivative, a hydroxyl, a haloalkyl, a dienophile, an aldehyde, a ketone, a sulfonyl halide, a thiol, an amine, a sulfhydryl, an alkene, an epoxide, and a phosphoramidite and is protected by a protecting group.

7. An oligonucleotide comprising:
   the quencher of claim 1;
   a minor groove binder (MGB); and
   a fluorophore.

8. The oligonucleotide of claim 7, wherein the fluorophore is at least one selected from coumarin, cyanine, BODIPY, fluorescein, rhodamine, pyrene, carbopyronine, oxazine, xanthene, thioxanthene, acridine, and a derivative thereof.

9. A composition for detecting a nucleic acid, comprising the oligonucleotide of claim 7.

10. A support for detecting a nucleic acid, comprising:
    the quencher of claim 1;
    a support; and
    a linker connecting the quencher and the support.

11. The support of claim 10, wherein the support is glass, cellulose, nylon, an acrylamide gel, dextran, polystyrene, or a resin.

12. The support of claim 10, wherein the linker is selected from a substituted or unsubstituted $C_1$-$C_{30}$ alkyl, a substituted or unsubstituted $C_2$-$C_{30}$ heteroalkyl including at least one heteroatom, a substituted or unsubstituted $C_6$-$C_{30}$ aryl, and a substituted or unsubstituted $C_3$-$C_{30}$ heteroaryl.

13. A method for detecting a nucleic acid, comprising:
    (a) preparing a reaction mixture including a target nucleic acid, a reagent needed to amplify the target nucleic acid, and the oligonucleotide of claim 7;
    (b) amplifying the target nucleic acid in the reaction mixture by a polymerase chain reaction; and
    (c) measuring the fluorescence intensity of the reaction mixture.

14. The method of claim 13, wherein the step (b) comprises:
    (b-1) elongating the oligonucleotide hybridized to the target nucleic acid by a polymerase;
    (b-2) separating a quencher and a fluorophore of the oligonucleotide from the target nucleic acid by an exonuclease activity of the polymerase; and
    (b-3) emitting fluorescence of the fluorophore which is cleaved from the quencher.

15. The method of claim 13, further comprising (d) measuring an amplification amount of the target nucleic acid from the fluorescence intensity measured in the step (c).

* * * * *

SEQUENCE LISTING

```
<160> NUMBER OF SEQ ID NOS: 10

<210> SEQ ID NO 1
<211> LENGTH: 10
<212> TYPE: DNA
<213> ORGANISM: Artificial
<220> FEATURE:
<223> OTHER INFORMATION: oligonucleotide for Compound 5-T10 according to
      Preparation Example 7

<400> SEQUENCE: 1
tttttttttt                                                                  10

<210> SEQ ID NO 2
<211> LENGTH: 12
<212> TYPE: DNA
<213> ORGANISM: Artificial
<220> FEATURE:
<223> OTHER INFORMATION: oligonucleotide for Compound 5-T12 according to
      Preparation Example 7

<400> SEQUENCE: 2
tttttttttt tt                                                               12

<210> SEQ ID NO 3
<211> LENGTH: 14
<212> TYPE: DNA
<213> ORGANISM: Artificial
<220> FEATURE:
<223> OTHER INFORMATION: oligonucleotide for Compound 5-T14 according to
      Prepartion Example 7

<400> SEQUENCE: 3
tttttttttt tttt                                                             14

<210> SEQ ID NO 4
<211> LENGTH: 16
<212> TYPE: DNA
<213> ORGANISM: Artificial
<220> FEATURE:
<223> OTHER INFORMATION: oligonucleotide for Compound 5-T16 according to
      Prepartion Example 7

<400> SEQUENCE: 4
tttttttttt tttttt                                                           16

<210> SEQ ID NO 5
<211> LENGTH: 18
<212> TYPE: DNA
<213> ORGANISM: Artificial
<220> FEATURE:
<223> OTHER INFORMATION: oligonucleotide for Compound 5-T18 according to
      Prepartion Example 7

<400> SEQUENCE: 5
tttttttttt tttttttt                                                         18

<210> SEQ ID NO 6
```

```
<211> LENGTH: 20
<212> TYPE: DNA
<213> ORGANISM: Artificial
<220> FEATURE:
<223> OTHER INFORMATION: oligonucleotide for Compound 5-T20 according to
      Prepartion Example 7

<400> SEQUENCE: 6
tttttttttt tttttttttt                                              20

<210> SEQ ID NO 7
<211> LENGTH: 26
<212> TYPE: DNA
<213> ORGANISM: Artificial
<220> FEATURE:
<223> OTHER INFORMATION: oligonucleotide correspnding b Actin according
      to Prepartion Example 8

<400> SEQUENCE: 7
atgccctccc ccatgccatc ctgcgt                                       26

<210> SEQ ID NO 8
<211> LENGTH: 26
<212> TYPE: DNA
<213> ORGANISM: Artificial
<220> FEATURE:
<223> OTHER INFORMATION: probe sequence for Experimental Example 2

<400> SEQUENCE: 8
atgccctccc ccatgccatc ctgcgt                                       26

<210> SEQ ID NO 9
<211> LENGTH: 30
<212> TYPE: DNA
<213> ORGANISM: Artificial
<220> FEATURE:
<223> OTHER INFORMATION: probe sequence for Experimental Example 3

<400> SEQUENCE: 9
tcagcaaatg catcacaaac agataatggc                                   30

<210> SEQ ID NO 10
<211> LENGTH: 30
<212> TYPE: DNA
<213> ORGANISM: Artificial
<220> FEATURE:
<223> OTHER INFORMATION: probe sequence for Experimental Example 4

<400> SEQUENCE: 10
tcagcaaatg catcacaaac agataatggc                                   30
```